(12) United States Patent
Kumbhani et al.

(10) Patent No.: US 7,125,563 B2
(45) Date of Patent: Oct. 24, 2006

(54) SUSTAINED RELEASE PHARMACEUTICAL PREPARATIONS AND METHODS FOR PRODUCING THE SAME

(75) Inventors: Davejibhai Kumbhani, Parsippany, NJ (US); Harish B. Pandya, Piscataway, NJ (US); Hiren Patel, Parsippany, NJ (US)

(73) Assignee: DAVA Pharmaceuticals, Inc., Fort Lee, NJ (US)

( * ) Notice: Subject to any disclaimer, the term of this patent is extended or adjusted under 35 U.S.C. 154(b) by 326 days.

(21) Appl. No.: 10/120,501

(22) Filed: Apr. 12, 2002

(65) Prior Publication Data

US 2003/0198670 A1 Oct. 23, 2003

(51) Int. Cl.
  *A61K 9/22* (2006.01)
  *A61K 9/24* (2006.01)
(52) U.S. Cl. ............... 424/468; 424/464; 424/472
(58) Field of Classification Search ........ 424/464–472, 424/473, 486, 480, 451, 456, 474, 494, 457, 424/488
See application file for complete search history.

(56) References Cited

U.S. PATENT DOCUMENTS

| | | | |
|---|---|---|---|
| 4,252,786 A * | 2/1981 | Weiss et al. ............... 424/19 |
| 4,264,573 A | 4/1981 | Powell et al. |
| 4,327,725 A | 5/1982 | Cortese et al. |
| 4,503,030 A | 3/1985 | Edgren et al. |
| 4,587,117 A | 5/1986 | Edgren et al. |
| 4,612,008 A | 9/1986 | Wong et al. |
| 4,695,591 A * | 9/1987 | Hanna et al. ............... 514/781 |
| 4,751,071 A | 6/1988 | Magruder et al. |
| 4,765,989 A | 8/1988 | Wong et al. |
| 4,777,049 A | 10/1988 | Magruder et al. |
| 4,783,337 A | 11/1988 | Wong et al. |
| 4,851,229 A | 7/1989 | Magruder et al. |
| 4,996,047 A * | 2/1991 | Kelleher et al. ............... 424/79 |
| 5,075,115 A * | 12/1991 | Brine et al. ............... 424/486 |
| 5,133,974 A * | 7/1992 | Paradissis et al. ........... 424/480 |
| 5,254,347 A | 10/1993 | Samejima et al. |
| 5,310,558 A | 5/1994 | Pozzi et al. |
| 5,445,829 A * | 8/1995 | Paradissis et al. ........... 424/480 |
| 5,464,633 A | 11/1995 | Conte et al. |
| 5,500,227 A | 3/1996 | Oshlack et al. |
| 5,514,384 A | 5/1996 | Signorino |
| 5,540,938 A | 7/1996 | Masterson et al. |
| 5,543,154 A | 8/1996 | Rork et al. |
| 5,543,155 A * | 8/1996 | Feket et al. ............... 424/473 |
| 5,580,580 A | 12/1996 | Masterson et al. |
| 5,662,933 A * | 9/1997 | Baichwal et al. ........... 424/457 |
| 5,674,895 A | 10/1997 | Guittard et al. |
| 5,681,582 A | 10/1997 | Gilis et al. |
| 5,681,585 A | 10/1997 | Oshlack et al. |
| 5,695,782 A | 12/1997 | Bourquin |
| 5,741,524 A | 4/1998 | Staniforth et al. |
| 5,753,265 A | 5/1998 | Bergstrand et al. |
| 5,780,055 A | 7/1998 | Habib et al. |
| 5,792,471 A | 8/1998 | Curatolo |

(Continued)

OTHER PUBLICATIONS

"Solutions / Buffer Solutions", USP 25, pp. 2340-2341.

(Continued)

*Primary Examiner*—Michael G. Hartley
*Assistant Examiner*—Micah-Paul Young
(74) *Attorney, Agent, or Firm*—Foley & Lardner LLP

(57) ABSTRACT

An extended release tablet comprising a core including albuterol sulfate and extended release agent; and an extended release coating on the core to provide for sustained release of the albuterol sulfate.

18 Claims, 6 Drawing Sheets

U.S. PATENT DOCUMENTS

| | | | |
|---|---|---|---|
| 5,807,580 A | 9/1998 | Luber | |
| 5,837,379 A | 11/1998 | Chen et al. | |
| 5,840,754 A | 11/1998 | Guittard et al. | |
| 5,858,412 A | 1/1999 | Staniforth et al. | |
| 5,912,268 A | 6/1999 | Guittard et al. | |
| 5,945,124 A | 8/1999 | Sachs et al. | |
| 5,958,456 A * | 9/1999 | Baichwal et al. | 424/89 |
| 6,024,982 A | 2/2000 | Oshlack et al. | |
| 6,124,355 A | 9/2000 | Guittard et al. | |
| 6,129,933 A | 10/2000 | Oshlack et al. | |
| 6,132,771 A | 10/2000 | Depui et al. | |
| 6,156,343 A | 12/2000 | Morita et al. | |
| 6,156,347 A | 12/2000 | Blatt et al. | |
| 6,183,777 B1 | 2/2001 | Chen et al. | |
| 6,210,710 B1 | 4/2001 | Skinner | |
| 6,210,714 B1 | 4/2001 | Oshlack et al. | |
| 6,217,903 B1 | 4/2001 | Skinner | |
| 6,245,351 B1 | 6/2001 | Nara et al. | |
| 6,251,430 B1 | 6/2001 | Zhang et al. | |
| 6,254,887 B1 | 7/2001 | Miller et al. | |
| 6,262,115 B1 | 7/2001 | Guittard et al. | |

OTHER PUBLICATIONS

"Physical Tests / Dissolution"; USP 24, pp. 1941-1951.

Alfonso R. Gennaro et al., *Remington's Pharmaceutical Sciences, Eighteenth Edition*, pp. 1684-1685 (1990).

Paul A. Steward, "Review of Pharmaceutical Controlled Release Methods and Devices" (1995).

Su H. Yum et al., "Chapter 3: Drug Delivery Systems Based on Diffusion and Osmosis", *CRC Controlled Drug Delivery—vol. 1: Basic Concepts*, pp. 8-11, and 65-87.

\* cited by examiner

SUSTAINED RELEASE PHARMACEUTICAL PREPARATIONS AND METHODS FOR PRODUCING THE SAME

BACKGROUND OF THE INVENTION

1. Field of the Invention

The present invention relates to sustained release pharmaceutical preparations and methods for producing the same. In particular, this invention relates to albuterol sulfate pharmaceutical sustained release formulations and their preparation.

2. Discussion of Background Information

Albuterol sulfate is a bronchodilator which is believed to be a beta-adrengenic agonist which stimulates beta-adrengeric receptor, which leads to relaxation of bronchial smooth muscle and inhibits hypersensitivity of mast cells. Albuterol sulfate is indicated for the relief of bronchospasm for the management of asthma and reversible obstructibe airway disease.

Albuterol sulfate is also known as, (±) ∝, -[(tert-butylamino)methyl]-4-hydroxy-m-xylene-∝,∝'-diol sulfate (2:1) salt, and has an empirical formula $(C_{13}H_{21}NO_3)_2 \cdot H_2SO_4$, a molecular weight of 576.7, and has the following structural formula:

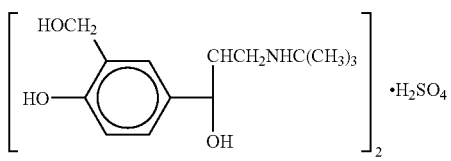

Albuterol sulfate extended release tablets are currently available as Volmax® Tablets, which are available in two strengths, 4 and 8 mg, and manufactured by Glaxo Wellcome Ltd. UK England, Muro Pharmaceutical Inc., Tewksbury, Mass. The oral administration of Volmax® tablets provides a duration of action up to 12 hours, with the maximum concentration of drug in plasma being reached within 6 hours, and the plasma half-life being about 9 hours. Volmax® releases the drug from polymeric coated tablets through a laser drilled hole on one side of the tablet (OROS™ technology). The tablets include a rate controlling semi-permeable membrane, and a core of albuterol and osmotic agent. An osmotic gradient caused by core components draws water only into the tablet, where albuterol and osmotic agent dissolve, and albuterol is released through the laser drilled hole.

As disclosed in U.S. Pat. No. 5,837,379, the disclosure of which is incorporated by reference herein in its entirety, extended release tablets containing osmotic tablets are known which have had an osmotically active drug core surrounded by a semi-permeable membrane. As disclosed therein, the core can be divided into two layers, one containing the active drug and the other containing a push layer of pharmacologically inactive ingredients which are osmotically active in the presence of gastrointestinal fluids. Also, as disclosed therein, an outer water permeable coating provided with an aperture covers the tablet to allow the drug to be pushed out of the tablet. Products of this type are disclosed in U.S. Pat. Nos. 4,327,725, 4,612,008, 4,751,071, 4,765,989, 4,777,049, 4,783,337 and 4,851,229. The disclosures of which are each incorporated by reference herein in their entireties.

U.S. Pat. No. 4,503,030, the disclosure of which is incorporated by reference herein in its entirety, discloses an osmotic device for delivering drugs to the stomach and the intestine. The device disclosed therein includes a shaped wall around a compartment described as a compartment which maintains its physical and chemical integrity in the stomach but loses its chemical and physical integrity in the intestine.

U.S. Pat. No. 4,587,117, the disclosure of which is incorporated by reference herein in its entirety, discloses an oral osmotic device which has a shaped wall which loses its integrity at a pH of 3.5 to 8.0, a passageway from a compartment to the exterior of the device.

U.S. Pat. No. 5,837,379, the disclosure of which is incorporated by reference herein in its entirety, also discloses the belief that its osmotic tablet operates by water passing through the membrane on the surface of the tablet which causes the core to swell and increase the pressure inside the tablet. This is disclosed to cause a very slight expansion of the partially hydrated core which is controlled by the use of a relatively small amount of water swellable polymer. It is disclosed that the expansion of the core will cause the membrane to open to relieve the internal pressure, and that once the initial opening or openings are formed, the swelling effect of the core components will cause the contents of the core to extrude through the initial opening without complete disintegration of the membrane. It is further disclosed that the internal pressure which is exerted on the membrane by the swelling and expanding osmotic core is relieved by the passage of the first portions of the core contents through the initial openings.

Moreover, sustained release tablets are known, such as disclosed in U.S. Pat. Nos. 5,500,227, 6,024,982 and 6,210,714, the disclosures of which are each incorporated by reference herein in their entireties, wherein release of the drug is controlled by means of the resistance of a coating layer or matrix against the diffusion of the drug therethrough. The release of drugs from such formulations is disclosed to be driven, e.g., by the gradient of the drug concentration resulting from penetration of, e.g., gastric fluid, by diffusion into the formulation.

Still further, U.S. Pat. No. 6,245,351, the disclosure of which is incorporated by reference herein in its entirety, discloses a drug-containing core coated with a coating composition containing a water-insoluble substance and a swellable polymer having no basis groups.

U.S. Pat. No. 5,254,347, the disclosure of which is incorporated by reference herein in its entirety, discloses a controlled release pharmaceutical preparation, comprising a core containing a pharmaceutically active ingredient, and a porous film of a hydrophobic polymeric substance or a hydrophobic polymeric substance and a hydrophilic polymeric substance, the core being coated with the porous film. It is further disclosed that the hydrophobic polymeric substance may be ethyl cellulose and that the hydrophilic polymer may be a water-soluble polymeric substance such as methyl cellulose.

U.S. Pat. Nos. 5,674,895, 5,840,754, 5,912,268, 6,124,355 and 6,262,115, the disclosures of which are each incorporated by reference herein in their entireties, disclose a dosage form for delivering oxybutynin in a rate-controlled dose.

SUMMARY OF THE INVENTION

The present invention is directed to extended release pharmaceutical preparations.

The present invention is also directed to methods for producing extended release pharmaceutical preparations.

The present invention provides a stable formulation of extended release tablets of albuterol in albuterol sulfate extended release tablets which are bioequivalent to Volmax® tablets, including the 4 and 8 mg tablets, manufactured by Glaxo Wellcome Muro Pharmaceutical Inc.

The present invention provides a diffusion controlled formulation that achieves bioequivalence to formulations utilizing osmotic devices.

The present invention is also directed to controlled release pharmaceutical preparations having desired dissolution rates that can be obtained in a diffusion controlled tablet.

The present invention provides an extended release tablet comprising a core including albuterol sulfate and extended release agent; and an extended release coating associated with the core to provide for sustained release of the albuterol sulfate.

The extended release agent can comprise a hydophobic polymer. The hydrophobic polymer can comprise ethyl cellulose.

The extended release coating can comprise hydrophobic polymer and hydrophilic polymer. The hydrophobic polymer can comprise ethyl cellulose and the hydrophilic polymer can comprise hi methyl cellulose.

The extended release coating can comprise ethyl cellulose and methyl cellulose, and the extended release agent can comprise ethyl cellulose.

The hydrophobic polymer and hydrophilic polymer of the extended release coating can be present in a weight ratio of 55–65:45–35 of the hydrophobic polymer to the hydrophilic polymer, preferably in a weight ratio of 57:43 of the hydrophobic polymer to the hydrophilic polymer.

The hydrophobic polymer and hydrophilic polymer of the extended release coating can comprise ethyl cellulose and methyl cellulose, respectively.

The extended release coating can have a weight of about 5 to 25 mg, more preferably about 8 to 13 mg.

Ethanol is preferably utilized as a solvent for preparing the core and the extended release coating.

The core can also include an anhydrous sulfate, such as calcium sulfate and/or lactose monohydrate.

The extended release tablet can have an albuterol dissolution profile for a formulation containing 8 mg of albuterol of:

| | |
|---|---|
| $2^{nd}$ Hour | Not more than 30% |
| $6^{th}$ Hour | 50–75% |
| $10^{th}$ Hour | Not less than 75%. |

The extended release tablet can have an albuterol dissolution profile for a formulation containing 4 mg of albuterol of:

| | |
|---|---|
| $2^{nd}$ Hour | Not more than 20% |
| $6^{th}$ Hour | 45–70% |
| $10^{th}$ Hour | Not less than 75%. |

The extended release tablet can have bioequivalency to an albuterol sulfate osmotic device formulation.

The present invention is also directed to a diffusion controlled tablet for extended release of albuterol sulfate comprising albuterol sulfate in a diffusion controlled formulation structured and arranged to provide an albuterol dissolution profile for a formulation containing 8 mg of albuterol of:

| | |
|---|---|
| $2^{nd}$ Hour | Not more than 30% |
| $6^{th}$ Hour | 50–75% |
| $10^{th}$ Hour | Not less than 75%. |

The present invention is also directed to a diffusion controlled tablet for extended release of albuterol sulfate comprising albuterol sulfate in a diffusion controlled formulation structured and arranged to provide an albuterol dissolution profile for a formulation containing 4 mg of albuterol of:

| | |
|---|---|
| $2^{nd}$ Hour | Not more than 20% |
| $6^{th}$ Hour | 45–70% |
| $10^{th}$ Hour | Not less than 75%. |

The present invention is also directed to a diffusion controlled formulation for extended release of albuterol sulfate comprising albuterol sulfate in a diffusion controlled formulation structured and arranged to provide bioequivalency to an albuterol sulfate osmotic device formulation.

The bioequivalency can be measured in a randomized, single dose, 2-way cross-over bioavailability study of healthy adult males under fasting conditions, based upon 36 individuals and plasma albuterol levels, for a formulation containing 4 mg of albuterol, and ln AUC 0-t is within 80–125% of 53074 pg.h/mL, ln AUCinf is within 80–125% of 55606 pg.h/mL, and ln Cmax is within 80–125% of 4383 pg/mL.

The bioequivalency can be measured in a randomized, single dose, 3-way cross-over bioavailability study of healthy adult males under fed and fasting conditions, based upon 16 individuals and plasma albuterol levels, for a formulation containing 8 mg of albuterol, and wherein, for fed adult males, ln AUC 0-t is within 80–125% of 106139 pg.h/mL, ln AUCinf is within 80–125% of 109692 pg.h/mL, and ln Cmax is within 80–125% of 7149 pg/mL.

The bioequivalency can be measured in a randomized, 2-way cross-over steady state bioavailability study of healthy adult males under fasting conditions, based upon 37 individuals and plasma albuterol levels, for a formulation containing 8 mg of albuterol, and wherein ln AUC 0-T is within 80–125% of 1125573 pg.h/mL and ln Cmax is within 80–125% of 14522 pg/mL.

BRIEF DESCRIPTION OF THE DRAWINGS

The present invention is further described in the detailed description which follows, in reference to the noted plurality of non-limiting drawings, wherein.

DETAILED DESCRIPTION OF THE INVENTION

Figure 1:
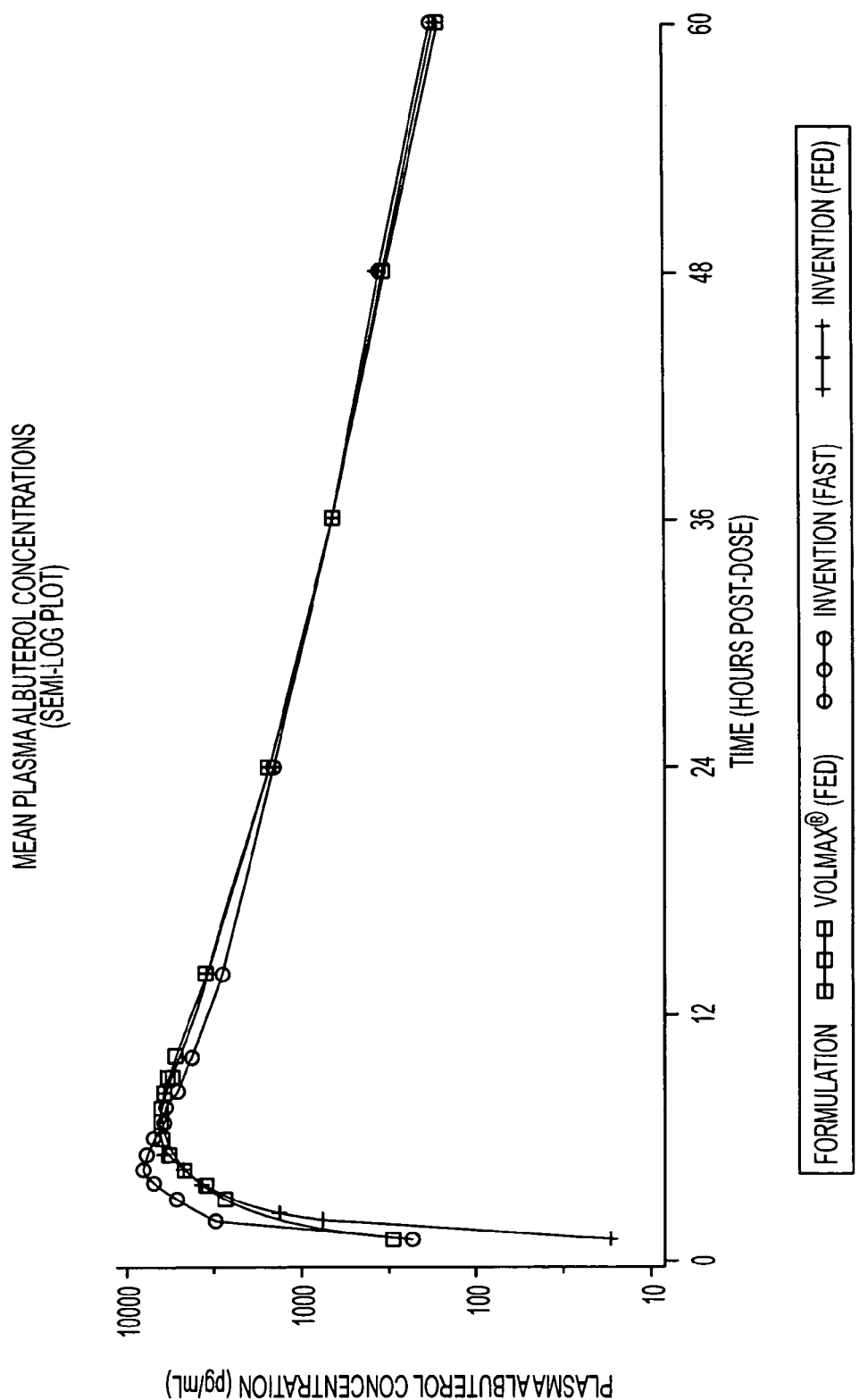
FIG. 1 shows a semi-log plot of mean plasma albuterol concentrations for plasma albuterol concentration vs. time for data shown in Table 16.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

All percent measurements in this application, unless otherwise stated, are measured by weight based upon 100% of a given sample weight. Thus, for example, 30% represents 30 weight parts out of every 100 weight parts of the sample.

Unless otherwise stated, a reference to a compound or component, includes the compound or component by itself, as well as in combination with other compounds or components, such as if mixtures of compounds.

Before further discussion, a definition of the following terms will aid in the understanding of the present invention.

Osmotic formulation device or osmotic tablet device is utilized herein to refer to formulations or tablets wherein one or more osmotic agents are configured and arranged to provide osmotic pressure or force associated with the formulation or tablet so as to cause active ingredient to be released from the formulation or tablet primarily due to the osmotic pressure or force, such as, but not limited to, pressure causing the active ingredient to be released by being pushed by pressure through an aperture in the formulation or tablet, or by causing pressure to expand a tablet layer.

Diffusion controlled is utilized herein to refer to formulations or tablets wherein the active ingredient is not released due to pressure or force, but is primarily released by diffusion according to Fick's laws.

Without being wished to be bound by theory, diffusion includes processes wherein molecules intermingle as a result of their kinetic energy of random motion. In contrast, osmosis is a selective diffusion process driven, e.g., forced, by the internal energy of the solvent molecules.

When referring to dissolution and dissolution profiles in the present specification and claims, the dissolution is performed utilizing the dissolution procedure set forth in the Examples, or a dissolution technique that is equivalent thereto.

As an overview, the present invention relates to extended (sustained) release pharmaceutical preparations. These preparations are especially useful for the extended release of albuterol sulfate. In particular, the present invention is directed to a tablet formulation including a core containing albuterol sulfate and an extended release agent; an extended release coating combining a hydrophilic agent and a hydrophobic agent; and can have one or more additional coatings. The core and extended release coating are formulated with respect to each other in order to provide a pharmaceutically acceptable in vitro dissolution profile, and particularly a dissolution profile and characteristics that are bioequivalent to that of albuterol obtainable with osmotic devices.

The tablet according to the present invention achieves desired dissolution in vitro profiles and bioequivalence to FDA approved albuterol tablet formulations, i.e., Volmax® tablets, in a tablet that is diffusion controlled as compared to being osmotically operated, such as Volmax® tablets.

In accordance with the present invention, the preferred percent of labeled amount of albuterol released at each specified time interval utilizing the dissolution test set forth in the Examples, for 8 mg albuterol tablets, is:

| | |
|---|---|
| 2$^{nd}$ Hour | Not more than 30% |
| 6$^{th}$ Hour | 50–75% |
| 10$^{th}$ Hour | Not less than 75% |

Moreover, in accordance with the present invention, the preferred percent of labeled amount of albuterol released at each specified time interval utilizing the dissolution test set forth in the Examples, for 4 mg albuterol tablets, is:

| | |
|---|---|
| 2$^{nd}$ Hour | Not more than 20% |
| 6$^{th}$ Hour | 45–70% |
| 10$^{th}$ Hour | Not less than 75% |

The moisture content of the tablet is preferably not more than 0.5 wt %. Moreover, residual alcohol content of alcohols utilized in preparing the formulation is preferably less than 0.5 wt %.

According to the present invention, the core includes the active pharmaceutical ingredient and an extended release agent. The active pharmaceutical ingredient preferably comprises albuterol sulfate.

The core according to the present invention preferably is prepared by a granulation process, with the granules containing the active pharmaceutical ingredient and the extended release agent. These granules preferably have an average particle diameter of about 125μ to 1700μ, more preferably about 180μ to 1000μ, and most preferably about 250μ to 600 μ.

The active pharmaceutical ingredient content of the core is preferably about 4 to 8 mg based upon active ingredient. For example, for albuterol sulfate, the content is the core would preferably be about 4.8 to 9.6 mg.

The core is preferably constructed to provide overall dosages of 4 or 8 mg of albuterol. The core is preferably formulated with 4.8 mg of albuterol sulfate to provide an overall dosage of 4 mg of albuterol, and the core is preferably formulated with 9.6 mg of albuterol sulfate to provide an overall dosage of 8 mg of albuterol. Thus, the tablet of the present invention can be described by either the amount of active ingredient contained therein, e.g., albuterol, or by pharmaceutically acceptable salts thereof, preferably albuterol sulfate.

The albuterol sulfate utilized in the formulation preferably has a particle size distribution, determined using a Malvern Mastersizer (Malvern 2600c with PS64 dry powder feeder, lens 100 mm obscuration 0.1 to 0.4) using particle in air method. Preferably, at least 50% of the particles of albuterol sulfate that are to be added to the core is not more than (NMT) 25 μm, and at least 90% is not more than 55 μm. Without wishing to be bound by theory, it is believed that particles within these parameters provide a good combination of dissolution and core hardness. Specific batches of albuterol sulfate tested had the following particle size distribution denoted in Table 1 below.

TABLE 1

Particle Size Distribution of Albuterol Sulfate

| | Sample 1 | Sample 2 | Sample 3 | Sample 4 |
|---|---|---|---|---|
| 50%, NMT 25 μm | 9% | 8% | 11% | 11% |
| 90%, NMT 55 μm | 24% | 22% | 31% | 32% |

The extended release agent can comprise one or more ingredients which in combination with the extended release coating control the release of the active pharmaceutical ingredient, especially albuterol sulfate, from the core in order to achieve a desired dissolution profile, and, in particular, bioequivalency with FDA approved formulations of albuterol sulfate. The extended release agent can comprise various water-insoluble materials, Examples of such water insoluble materials include hydrophobic polymers including, but are not limited to, one or more of ethyl cellulose, butyl cellulose, cellulose acetate, cellulose propionate, polyvinyl acetate, polyvinyl butyrate, ethyl acrylate-methyl methacrylate-ethyl ammonium trimethyl chloride methacrylate copolymer and N-vinyl-2-pyrrolidonecellulose ether, cellulose ester, polyvinyl ester, acrylic acid type polymer having a quaternary ammonium-alkyl group, and Plasdone® K-90, Povidone, homopolymer of N-vinyl-2-pyrrolidone. Preferably, the extended release agent comprises one or more of ethyl cellulose, butyl cellulose, cellulose acetate, cellulose propionate, polyvinyl acetate, polyvinyl butyrate, ethyl acrylate-methyl methacrylate-ethyl ammonium trimethyl chloride methacrylate copolymer and N-vinyl-2-pyrrolidone. Most preferably, the extended release agent comprises ethyl cellulose, such as Ethocel N-10 which is obtainable from Dow Chemical, Midland, Mich.

The core can be prepared in any manner, such as by utilizing any conventional manufacturing technique. Thus, the core can be produced by combining the active pharmaceutical ingredient and at least one agent capable of restricting release of the active ingredient with each other, and other ingredients. For example, the core may contain a wide variety of excipients, such as those ingredients that are conventionally included in the core of tablets, including diluents, glidents, binders, granulating solvent, granulating agents, anti-aggregating agents, buffers, lubricants.

For example, diluents can include, but are not limited to, one or more of sugars such as sucrose, lactose, mannitol, glucose; starch; microcrystalline cellulose; sorbitol, maltodextrin, whey, calcium phosphate; calcium sulfate; sodium sulfate or similar anhydrous sulfate; calcium lactate; lactose anhydrous; and lactose monohydrate. Preferably, the diluents comprise calcium sulfate and/or lactose monohydrate. Preferably, lactose anhydrous is not included in the core, because of its ability to absorb water from solvents, such as ethanol, thereby contributing to undesirable weight gain.

Examples of binders include, but are not limited to, one or more of polyvinyl alcohol, polyacrylic acid, polymethacryic acid, polyvinyl pyrrolidone, sucrose, sorbitol, hydroxyethyl cellulose, hydroxypropylmethyl cellulose, hydroxypropyl cellulose, polyethylene glycols, gum arabic, gelatin, agar, starch, etc.

Lubricants and anti-aggregating agents include, but are not limited to, one or more of talc, magnesium stearate, calcium stearate, colloidal silica, stearic acid, waxes, hydrogenated vegetable oil, polyethylene glycols, sodium benzoate, sodium laurylsulfate, magnesium laurylsulfate and dl-leucine. Preferably, the lubricants include stearic acid and/or magnesium stearate.

Solvents include, but are not limited to, one or more of acetone, ethanol, isopropyl alcohol (IPA) and/or methylene chloride. Preferably, the solvent for the core comprises ethanol. The use of chlorinated solvents, such as methylene chloride is preferably avoided. Therefore, the tablets preferably do not contain a chlorinated solvent, such as methylene chloride. The amount of solvent can be adjusted to provide a sufficient amount to achieve the formation of granules while not being of such a high amount as to turn the mixture into a large mass instead of granular in nature. Moreover, it is preferred to control the solvent addition time to effect adequate granulation. It is preferred that the temperature of granulating solution is preferably not be more than 26° C. at the time of addition to avoid lumping.

The ingredients can be combined and/or granulated in one or more procedures utilizing any appropriate techniques, such as by granulating in a low shear granulator, fluidized bed granulation, high shear granulator.

It is noted that during development of granulation, formulations were prepared with and Without the use of calcium sulfate to study its impact on dissolution profile of the product. Based on a fast drug release of albuterol sulfate from tablets without calcium sulfate, it is preferred that calcium sulfate be incorporated in the core to control drug release from the tablets.

Following production of the granules for the core, the granules are dried under sufficient conditions to provide granules preferably having not more than 0.5 wt % alcohol, and preferably not more than 0.5 wt % water. Therefore, for commercial batches, it is preferred that the batches be dried at a preferred temperature of at about 50° C. preferably for at least 16 hours to ensure solvent removal, such as ethanol and/or water.

The cores are compressed into tablets to a hardness of preferably between about 2 and 6 kP, with a preferred value being about 4 kP.

The extended release coating is deposited on the tablets in a location that is external to the core, and is preferably layered directly onto the core. The extended release coating is formulated to provide in conjunction with the extended release agent in the core a desired dissolution profile, and bioequivalency to commercially available albuterol sulfate tablet formulations, such as Volmax® tablets.

The extended release coating comprises a film preferably a combination of hydrophobic and hydrophilic polymers. Preferably, the active pharmaceutical ingredient, which is preferably albuterol sulfate, is not present in the extended release coating. In this regard, preferably the active a pharmaceutical ingredient, which is preferably albuterol sulfate, is only present in the core.

The hydrophobic polymer constituting the film is not particularly limited, provided that it has film forming ability, and is insoluble in water, but soluble in a water-miscible organic solvent. Examples of hydrophobic polymers include, but are not limited to, one or more of ethyl cellulose, butyl cellulose, cellulose acetate, cellulose propionate, polyvinyl acetate, polyvinyl butyrate, ethyl acrylate-methyl methacrylate-ethyl ammonium trimethyl chloride methacrylate copolymer and N-vinyl-2-pyrrolidonecellulose ether, cellulose ester, polyvinyl ester, acrylic acid type polymer having a quaternary ammonium-alkyl group, and Plasdone® K-90, Povidone, homopolymer of N-vinyl-2-pyrrolidone. Preferably, there may be included, for example, ethyl cellulose, butyl cellulose, cellulose acetate, cellulose propionate, polyvinyl acetate, polyvinyl butyrate, ethyl acrylate-methyl methacrylate-ethyl ammonium trimethyl chloride methacrylate copolymer and N-vinyl-2-pyrrolidone. Most preferably, the hydrophobic polymeric substance comprises ethyl cellulose, such as Ethocel N-10, which is obtainable from Dow Chemical, Midland, Mich.

The hydrophilic polymer maybe a water-soluble polymeric substance, including, but are not limited to, one or more of methyl cellulose, polysaccharides optionally having a sulfuric acid group such as pullulan, dextrin, alkali metal alginate, etc.; polysaccharides having a hydroxy-alkyl group or a carboxyalkyl group such as hydroxypropyl cellulose, hydroxypropylmethyl cellulose, carboxymethyl cellulose sodium, etc.; methyl cellulose, polyvinyl pyrrolidone, polyvinyl alcohol or polyethylene glycol, etc. may be included. Preferably, the hydrophilic polymeric substance comprises methyl cellulose, such as Methocel E-15, which is obtainable from Dow Chemical, Midland, Mich.

Changing the weight ratio of hydrophobic polymer to hydrophilic polymer in the extended release coating affects the dissolution of the albuterol from the tablet. Therefore, the weight ratio of hydrophobic polymer to hydrophilic polymer can be varied for each specific formulation to obtain desired dissolution profiles for the formulation. Preferable weight ratios for the hydrophobic polymer to hydrophilic polymer include weight ratios of 55–65:45–35, with one preferred weight ratio of hydrophobic polymer to hydrophilic polymer being 57:43.

The solvent for the extended release coating can comprise various solvents including, but are not limited to, acetone, ethanol, isopropyl alcohol (IPA) and/or methylene chloride. Preferably, the solvent for the extended release coating comprises ethanol. The use of chlorinated solvents, such as methylene chloride is preferably avoided. Various combinations of solvents can be used, such as, but not limited to, ethanol and isopropyl alcohol, and combinations of isopropyl alcohol:water, denatured alcohol:water and ethyl alcohol:water.

Tablets prepared using isopropyl alcohol were found to have a drug release that is slower than when ethanol is used as coating solvent. In addition, when isopropyl alcohol is used for both, granulation and coating, the drug release is found to be slower compared to that of the product made using ethanol for granulation and coating. Accordingly, ethanol is a preferred solvent for both granulation and coating.

To obtain a product that is bioequivalent to Volmax®, the hydrophobic polymer and the hydrophilic polymer are blended with each other to provide an extended release coating that has desired dissolution profiles and/or bioequivalence properties in conjunction with the extended release agent and active ingredient included in the core. For example, using the preferred formulations as disclosed herein, a weight ratio of 57 parts by weight of Ethocel N-10 to 43 parts by weight of Methocel E-15, a coating weight gain of about 5–25 mg per tablet is preferred. Preferably, a coating weight gain of 20 mg per tablet, for 4 mg and 8 mg tablets, using R&D equipment provides a drug release profile similar to that of Volmax® tablets. Commercial tablets preferably have a weight gain of 8.7 and 12.4 mg, respectively, for 4 mg and 8 mg albuterol sulfate tablets. A preferred weight gain for the extended release coating is about 5 to 25 mg, more preferably about 8 to 13 mg.

Coating of the extended release coating can be performed using various techniques, such as conventional coating techniques such as perforated pan, or using fluidized bed technique. These methods are commonly understood by individuals who are practicing the art tablet manufacture. The angle of spray guns utilized in spayed on the coating can be varied, such as, but not limited to between 30° and 75°, with one preferred angle being 65°.

Without being wished to be bound by theory, it is believed that the hydrophilic polymer provides a porous layer for diffusion of the active ingredient from the core. In this regard, the hydrophilic polymer is believed to be dissolved to leave pores through which diffusion takes place.

In the formulation of the present invention, by adequately controlling the weight of the extended release coating, and the ratio of hydrophobic polymer to hydrophilic polymer as well as the extended release agent in the core, it is possible to make a tablet having a desired in vitro dissolution rate. For example, and without wishing to be bound by theory, when the pharmaceutically active ingredient contained in the core is a drug which is desired to exhibit a pharmaceutical effect within a short period of time after administration, it is preferred to make the film thinner and the porosity thereof greater upon dissolving of the hydrophilic polymeric substance, while in the case of a drug which is desired to be released persistently for a prolonged period of time, it is preferred to make the film thicker and the porosity thereof smaller upon dissolving of the hydrophilic polymeric substance.

For a set composition for the extended release coating, a difference in dissolution rate of the active pharmaceutical ingredient can be obtained by varying the weight of the coating. Thus, a higher coating weight of the extended release coating provides for a greater time to dissolve an equivalent concentration of active pharmaceutical ingredient as compared to a lower weight of the extended release coating. Therefore, the weight of the extended release coating is preferably accurately monitored during production of the tablet to ensure a desired dissolution rate for an extend release coating composition. For example, the weight of the extended release coating can be monitored by determining core weight prior to applying the extended release coating, and then determining the total weight of the core and extended release coating. The difference between these two values would be the weight gain due to the extended release coating. For example, a weight gain of 10 mg would provide a slower dissolution rate than a weight gain of 9 mg.

The tablet can include optional coatings, such as coatings to provide cosmetic elegance and/or to facilitate packaging of the product. For example, an optional coating can comprise a color coating including, but not limited to, Opadry Green. Another optional coating can include, for example, a clear solution, such as, but not limited to, Opadry Clear. These optional coatings can be utilized in combination, such as a clear coat being applied over a color coating.

The active pharmaceutical ingredient according to the present invention preferably comprises albuterol sulfate, but can comprise other active ingredients. However, the present invention is particularly suited to albuterol sulfate as the active pharmaceutical ingredient. In this regard, as noted above, the present invention provides for the extended release of albuterol sulfate having similar dissolution profiles to that of pharmaceutical tablets operating on osmotic principles and provides bioequivalency thereto.

The present invention will be further illustrated by way of the following Examples. These Examples are non-limiting and do not restrict the scope of the invention.

Unless stated otherwise, all percentages, parts, etc. presented in the examples are by weight.

EXAMPLES

The following procedures are utilized in connection with the present invention:

A. Dissolution Procedure—For Determining Dissolution Rates and Profiles in Accordance with the Present Invention:

The dissolution procedure utilized in connection with the present invention includes the following:

The dissolution apparatus is a Van Kel Model VK-7000 utilized according to USP 24, Method <724>. The dissolution units have paddle shafts or equivalent dissolution unit to meet USP 24 Method <711> criteria on six samples, and using an HPLC system equipped with UV detector. The following reagents and standards are used in the dissolution procedure:

Reagents and Standards:

| | |
|---|---|
| Water | Purified water |
| Sodium Chloride | ACS reagent |
| 1-Octane sulfonic acid sodium salt | Reagent Grade |
| Ammonium acetate | ACS reagent |
| 2-Propanol | HPLC grade |
| Methanol | HPLC grade |
| Glacial Acetic Acid | ACS reagent |
| Albuterol Sulfate | Standard with known purity or USP RS |

Preparation of Dissolution Medium:

Dissolve 9.0 grams of sodium chloride in 1000 mL of water, heat to 37° C.±0.5° C., filter and degas, to thereby form 0.9% sodium chloride solution.

Preparation of Mobile Phase:

Dissolve 600 mg of 1-Octane sulfonic acid sodium salt, and 20.0 g of ammonium acetate into 920 mL of water. Add 30 mL of 2-propanol, 10 mL of methanol, and 40 mL of glacial acetic acid, mix well.

Filter with vacuum and degas by sonication for 5 minutes. Helium sparging is also suitable.

Preparation of Standard Solution:

A. Stock Standard Solution:

Accurately weigh about 24 mg of albuterol sulfate, and transfer quantitatively into 100 mL volumetric flask with the aid of about 50 mL dissolution medium. Dissolve the standard by sonication, dilute with dissolution medium to volume, and mix.

B. Working Standard Solution:

Pipet 4.0 mL of stock standard solution into a volumetric flask, a 200 ml volumetric flask for 4 mg tablet, and a 100 mL volumetric flask for 8 mg tablet.

Dilute with dissolution medium to volume and mix.

Filter a portion of the solution through nylon disk filter of 0.45 μm porosity SRI (Scientific Resources, Inc. catalog: #44525-NC) or equivalent, discarding a first few mL. Fill 1 mL HPLC glass vials with the filtered material.

Chromatographic System for Dissolution Measurement:

Prepare a liquid chromatographic system according to Table 2 below:

TABLE 2

Chromatographic System for Dissolution Measurement: Equipment and Conditions:

| | |
|---|---|
| Column | Symmetry C18, 5 μm, 3.9 × 150 mm, Waters catalog # WAT 046980, which represents USP packing L1 type or equivalent |
| Column Temperature | Thermostatically controlled at 30° C. |
| Flow Rate | 1.0 mL per minute using a Waters 600 series pump or equivalent |
| Detector | UV at 276 nm using a Waters 486 or equivalent |
| Integrator | Waters Millennium System or equivalent |
| Injector Volume | 50 μL with a Waters Model 717 or an equivalent autosampler |
| Retention Time | About 5 minutes |
| Run Time | 8 minutes |

The dissolution tests are performed using 900 mL of dissolution medium (0.9% sodium chloride solution) and a paddle rotational speed of 50 rpm, and sampling is conducted in accordance with USP 24 Method <711>. For each withdrawal of 10 mL of sample for testing, 10 mL of dissolution medium preheated to 37° C.±0.5° C. is added to the dissolution vessel thereby replacing the withdrawn dissolution solution.

Analysis of the samples is performed using standard HPLC techniques to conform the average value of the following parameters to:

The relative standard deviation (RSD) of albuterol peak area response for replicate injections should not be more than 3.0%.

The tailing factor for albuterol peak area should not be more than 2.0.

The number of theoretical plates per column for albuterol peak should not be less than 2000.

Particle size and powder fineness can be determined using sieve analysis according to USP-23 NF 18, such as by using an ATM Sonic Sifter Model L3P.

EXAMPLES 1–7

The following Tables 3 and 4 illustrate formulations of 4 and 8 mg tablets according to the present invention which were used in the Examples which follow.

TABLE 3

ALBUTEROL SULFATE ER TABLETS, 4 MG AND 8 MG

| Strength | 8 mg | 4 mg | 4 mg | 8 mg | 8 mg | 8 mg | 8 mg | 4 mg | 4 mg |
|---|---|---|---|---|---|---|---|---|---|
| Example # | Example-I | Example-I | Example-II A | Example-III | Example-IV | Example-V | Example-V | Example-VI B | Example VI C |
| Ingredients (in mg) | | | | | | | | | |
| I CORE | | | | | | | | | |
| Albuterol Sulfate USP | 9.60 | 4.80 | 4.80 | 9.60 | 9.60 | 9.60 | 9.60 | 4.80 | 4.80 |
| Lactose monohydrate NF | 66.00 | 70.80 | 70.80 | 74.40 | 66.00 | 66.00 | 66.00 | 70.80 | 70.80 |

TABLE 3-continued

ALBUTEROL SULFATE ER TABLETS, 4 MG AND 8 MG

| Strength<br>Example #<br>Ingredients (in mg) | 8 mg<br>Example-I | 4 mg<br>Example-I | 4 mg<br>Example-II A | 8 mg<br>Example-III | 8 mg<br>Example-IV | 8 mg<br>Example-V | 8 mg<br>Example-V | 4 mg<br>Example-VI B | 4 mg<br>Example VI C |
|---|---|---|---|---|---|---|---|---|---|
| powder | | | | | | | | | |
| Calcium Sulfate powder USP | 8.40 | 8.40 | 8.40 | — | 8.40 | 11.40 | 15.07 | 8.40 | 8.40 |
| Ethocel N-10 premium | 12.50 | 12.50 | 13.00 | 12.50 | — | 9.17 | 5.83 | 13.00 | 13.00 |
| Ethocel N-10 premium | 2.00 | 2.00 | 1.50 | 2.00 | — | 2.00 | 2.00 | 1.50 | 1.50 |
| PVP K-90 | — | — | — | — | 14.50 | — | — | — | — |
| Isopropyl alcohol USP | — | — | 15.00* | — | — | — | — | — | — |
| Ethyl alcohol, 95% USP | *15.00 | *15.00 | n/a | *20.0 | *20.0 | *20.0 | *20.0 | — | 15.00* |
| Denatured Alcohol (SDA-3A) | — | — | — | — | — | — | — | 15.00* | — |
| Stearic Acid NF | 1.00 | 1.00 | 1.00 | 1.00 | 1.00 | 1.00 | 1.00 | 1.00 | 1.00 |
| Magnesium Stearate NF | 0.50 | 0.50 | 0.50 | 0.50 | 0.50 | 0.50 | 0.50 | 0.50 | 0.50 |
| Total (Solids in mg) | 100.00 | 100.00 | 100.00 | 100.00 | 100.00 | 99.67 | 100.00 | 100.00 | 100.00 |
| II ER Coating solution | | | | | | | | | |
| Methocel E-15 premium | 8.325 | 8.325 | 2.14 | 4.20 | 4.20 | 4.00 | 4.00 | 2.14 | 2.14 |
| Ethocel N-10 premium | 11.25 | 11.25 | 2.88 | 4.20 | 4.20 | 5.40 | 5.40 | 2.88 | 2.88 |
| Triacetin USP | 2.50 | 2.50 | 0.64 | 1.00 | 1.00 | 1.20 | 1.20 | 0.64 | 0.64 |
| Purified water USP | 32.50* | 32.50* | *8.40 | *13.33 | *13.33 | *15.0 | *15.0 | *8.40 | *8.40 |
| Ethyl alcohol USP | 292.50* | 292.50* | *74.67 | *113.33 | *113.33 | *134.0 | *134.0 | *74.67 | *74.67 |
| Total (Solids in mg) | 22.075 | 22.075 | 5.66 | 9.40 | 9.40 | 10.60 | 10.60 | 5.66 | 5.66 |
| III White F/C suspension and clear solution | | | | | | | | | |
| Opadry white YS-1-7003 | ***1.67 | ***1.67 | 1.65 | 1.67 | 1.67 | 2.00 | 2.00 | 1.65 | 1.65 |
| Purified water USP | 16.67* | 16.67* | 16.67* | *16.67 | *16.67 | *20.00 | *20.00 | 16.67* | 16.67* |
| Opadry clear YS-1-7006 | 0.167 | 0.167 | 0.17 | 0.167 | 0.167 | 0.20 | 0.20 | 0.17 | 0.17 |
| Propylene Glycol USP | 0.167 | 0.167 | 0.17 | 0.167 | 0.167 | 0.20 | 0.20 | 0.17 | 0.17 |
| Purified water USP | 8.33* | 8.33* | 8.33* | *8.33 | *8.33 | *10.0 | *10.0 | 8.33* | 8.33* |
| Carnuba wax Powder NF | 0.167 | 0.167 | 0.1 | 0.167 | 0.167 | 0.20 | 0.20 | 0.1 | 0.1 |
| Total (Solids in mg) | 2.171 | 2.171 | 2.11** | 2.171 | 2.171 | 2.60 | 2.60 | 2.11** | 2.11** |

TABLE 4

ALBUTEROL SULFATE ER TABLETS, 4 MG 4 mg

| Control #<br>Ingredients (in mg) | Example-VII A | B | C | D |
|---|---|---|---|---|
| I CORE | | | | |
| Albuterol Sulfate USP | 4.80 | | | |
| Lactose monohydrate NF powder | 70.80 | | | |
| Calcium Sulfate powder USP | 8.40 | | | |
| Ethocel N-10 premium | 12.50 | | | |
| Ethocel N-10 premium | 2.00 | | | |
| Isopropyl alcohol USP | | | | |
| Ethyl alcohol, 95% USP | *15.00 | | | |
| Stearic Acid NF | 1.00 | | | |
| Magnesium Stearate NF | 0.50 | | | |
| Total (Solids in mg) | 100.00 | | | |
| II ER Coating solution | | | | |
| Methocel E-15 premium | 1.56 | 3.12 | 4.68 | 5.475 |
| Ethocel N-10 premium | 14.08 | 12.52 | 10.96 | 10.165 |
| Triacetin USP | 2.00 | 2.00 | 2.00 | 2.00 |
| Purified water USP | 26.00* | 26.00* | 26.00* | 26.00* |
| Ethyl alcohol USP | 234.00* | 234.00* | 234.00* | 234.00* |
| Total (Solids in mg) | 17.64 | 17.64 | 17.64 | 17.64 |
| III White F/C suspension and clear solution | | | | |
| Opadry green | 1.67 | 1.67 | 1.67 | 1.67 |
| Purified water USP | *16.67 | *16.67 | *16.67 | *16.67 |
| Opadry clear YS-1-7006 | 0.167 | 0.167 | 0.167 | 0.167 |
| Propylene Glycol USP | 0.167 | 0.167 | 0.167 | 0.167 |
| Purified water USP | *8.33 | *8.33 | *8.33 | *8.33 |
| Carnauba wax Powder NF | 0.167 | 0.167 | 0.167 | 0.167 |
| Purified water USP | | | | |
| Total (Solids in mg) | 2.171 | 2.171 | 2.171 | 2.171 |

*= Ingredient will be removed
**= Blue and Yellow dye were mixed in formula
***= opadry green instead of Opadry white The following procedure is utilized to produce tablets according to the present invention unless otherwise stated:

Core Preparation

Screen ingredients including lactose monohydrate, albuterol sulfate and calcium sulfate through #18 mesh and the extended release agent (Ethocel N-10) through #12 mesh. The ingredients are mixed in a twin shell blender without I-bar to a uniform blend. The contents are emptied into an AMF mixer and set at 45±5 RPM.

Prepare a solution of the extended release agent (Ethocel N-10, 2 kg.) in of warm (50° C.±5° C.) solvent (Ethyl Alcohol). Stir the solution until clear, such as for a minimum time of one hour. Then, cool the solution to not more than 26° C. Start the mixer and pump the Ethocel N-10 solution to granulate ingredients, such as by delivering the solution over a period of three minutes. Mix to achieve adequate granulation, such as for about 6 to 9 minutes. Dry by spreading, such as on a stainless steel tray at 50° C.±5° C. for not more than 16 hours and until the average loss on drying at 75° C. is less than 0.5%.

Mill the dried granulation in a Fitzmill having screw-feeder, perforated Stainless Steel plate #0065, set for medium speed, knives forward and feeder at 3.5±0.5 kg.

Screen remaining ingredients of the stearic acid and magnesium stearate through #18 mesh and collect in a suitable container. Transfer milled granulation, screened ingredients through twin shell without I-bar blender, and blend until uniform, preferably about 5 minutes.

Set the tablet press for ¼" round, deep concave, plain tooling, and compress the blend at a nominal value of at 100 mg±7 mg. Compress at 4 kp (range 2–6 kp) hardness. The cores in these examples are at a thickness and 0.130"–0.155", and have a friability less than 1%.

Preparation of Extended Release Coating Solution

Prepare Extended Release (ER) coating solution by dissolving Methocel E-15 and Ethocel N-10 in a mixture of ethyl alcohol and purified water, mixing until clear, such as for a minimum of 5 hours. Add Triacetin and stir for preferably 15 more minutes to equally distribute. Store this solution for minimum time of 10 hours before application, such as 15 to 16 hours.

Preparation of Film Coating Solutions

Prepare film coating colored solution using Opadry Green and purified water, stirring the suspension until dispersed, such as for 2 hours.

Prepare film coating clear solution using Opadry Clear and purified water, stirring the suspension until dispersed and clear, such as for 2 hours.

Add Propylene Glycol into the solution and stir for 15 more minutes.

Coating Core with Extended Release Coating Solution

Transfer the core tablets into a 48" perforated pan. Set spray guns at 65° angle, and adjust the atomizing air pressure at 25 PSI atomizing air pressure. Set the pump for extended release coating solution to provide solution at 130 ml/min/gun (RANGE: 100–130 ml/min/gun). Set the air temperature at 75° C. or less to warm the core tablets. Turn the coating pan at 6 RPM pan speed (range 4–8 RPM). Dry the extended release solution coated tablets for 30 minutes at 70° C.±5° C. inlet air temperature. Determine the coating weight gain.

Coating with Film Coating Solutions

Apply coatings as above, except liquid rate is at 90±15 ml/min/gun. Dry the tablets for 10 minutes at 70° C.±5° C. Determine the coating weight gain.

Example 1

Example 1 is directed to an 8 mg tablet produced utilizing the ingredients and processes indicated above and in Table 3. Dissolution testing was performed using the dissolution procedure as discussed above. The coating weight ratio of Ethocel E-10 to Methocel E-15 was 57:43 in this example. The results are illustrated in Table 5 below. In particular, the release of albuterol sulfate in the tablet according to the present invention was found to be comparable to that of the commercial product.

Table 3 also shows an example of a formulation of a 4 mg tablet according to the present invention.

TABLE 5

|  | Time, Hrs | | | | | |
| --- | --- | --- | --- | --- | --- | --- |
|  | 1 | 2 | 4 | 6 | 8 | 10 |
| Invention, 8 mg | 0 | 11 | 54 | 74 | 87 | 94 |
| Volmax ®, 8 mg | 10 | 22 | 47 | 70 | 86 | 93 |

Example 2

Example 2 is directed to a 4 mg tablet produced utilizing the ingredients and processes indicated above and in Table 3. Dissolution testing was performed using the dissolution procedure as discussed above. In particular, this example is similar to that of Example 1 with isopropyl alcohol being used instead of ethyl alcohol in granulation and coating, and a 4 mg formulation being utilized. The results are illustrated in Table 6 below. The release of albuterol sulfate in the tablet according to the present invention was found to be slower than the commercial product.

TABLE 6

|  | Time, Hrs | | | | | |
| --- | --- | --- | --- | --- | --- | --- |
|  | 1 | 2 | 4 | 6 | 8 | 10 |
| Invention, 4 mg | 1 | 5 | 38 | 62 | 79 | 89 |
| Volmax ®, 4 mg | 8 | 22 | 47 | 69 | 87 | 92 |

Example 3

Example 3 is directed to an 8 mg tablet produced utilizing the ingredients and processes indicated above and in Table 3. Dissolution testing was performed using the dissolution procedure as discussed above. In particular, this example is similar to that of Example 1 with $CaSO_4$ being omitted, and the amount of lactose monohydrate being correspondingly increased to bring the core to 100 mg. The results are illustrated in Table 7 below. The coating weight ratio of Ethocel E-10 to Methocel E-15 was 50:50 in this example. The release of albuterol sulfate in the tablet according to the present invention was found to be faster than the commercial product.

TABLE 7

|  | Time, Hrs | | | | | |
| --- | --- | --- | --- | --- | --- | --- |
|  | 1 | 2 | 4 | 6 | 8 | 10 |
| Invention, 8 mg | 28 | 51 | 80 | 96 | 100 | 101 |
| Volmax ®, 8 mg | 10 | 22 | 47 | 70 | 86 | 93 |

Example 4

Example 4 is directed to an 8 mg tablet produced utilizing the ingredients and processes indicated above and in Table 3. Dissolution testing was performed using the dissolution procedure as discussed above. In particular, this example is similar to that of Example 1 with PVP K-90 replacing Ethocel N-10 as binder. The coating weight ratio of Ethocel E-10 to Methocel E-15 was 50:50 in this example. For tablets having the same thickness of Example 1, the hardness was found to be 12 Kp. The results are illustrated in Table 8 below. The release of albuterol sulfate in the tablet according to the present invention was found to be faster than the commercial product.

TABLE 8

|  | Time, Hrs | | | | | |
| --- | --- | --- | --- | --- | --- | --- |
|  | 1 | 2 | 4 | 6 | 8 | 10 |
| Sidmak, 8 mg | 4 | 25 | 65 | 87 | 98 | 100 |
| Volmax ®, 8 mg | 10 | 22 | 47 | 70 | 86 | 93 |

Example 5

Example 5 is directed to an 8 mg tablet produced utilizing the ingredients and processes indicated above and in Table 3. Dissolution testing was performed using the dissolution procedure as discussed above. In particular, this example is similar to that of Example 1 with a portion of Ethocel N-10 in granulation being replaced with $CaSO_4$. The results are illustrated in Table 9 below. The release of albuterol sulfate in the tablet according to the present invention was found to be faster than the commercial product.

TABLE 9

|  | Time, Hrs | | | | | |
| --- | --- | --- | --- | --- | --- | --- |
|  | 1 | 2 | 4 | 6 | 8 | 10 |
| Invention, 8 mg | 10 | 40 | 72 | 91 | 98 | 100 |
| Volmax ®, 8 mg | 10 | 22 | 47 | 70 | 86 | 93 |

Example 6

Example 6 is directed to a 4 mg tablet produced utilizing the ingredients and processes indicated above and in Table 3. Dissolution testing was performed using the dissolution procedure as discussed above. In particular, this example is similar to that of Example 1 with core tablets being manufactured using denatured alcohol (100 parts by weight of ethyl alcohol, 95% USP and 5 parts by weight of methyl alcohol, USP) instead of ethyl alcohol. The results are illustrated in Table 10 below. The release of albuterol sulfate in the tablet according to the present invention was found to be comparable to that using ethyl alcohol.

TABLE 10

|  | Time, Hrs | | | | | |
| --- | --- | --- | --- | --- | --- | --- |
|  | 1 | 2 | 4 | 6 | 8 | 10 |
| Invention, Denatured alcohol, 4 mg | 29 | 53 | 84 | 96 | 97 | 97 |
| Invention, ethyl alcohol, 4 mg | 31 | 57 | 87 | 97 | 99 | 99 |

Example 7

Example 7 is directed to 4 mg tablets produced utilizing the ingredients and processes indicated above and in Table 4. Dissolution testing was performed using the dissolution procedure as discussed above. In particular, this example is similar to that of Example 1 with core tablets being coated with varying weight ratios of Ethocel N-10 and Methocel E-15, as indicated in Table 4 and indicated below, as follows:

Tablets were coated with extended release coating suspension having—

|  | Methocel Ethocel weight ratio of: |
| --- | --- |
| A | 10:90 |
| B | 20:80 |
| C | 30:70 |
| D | 35:65 |

The extended release coating for all four ratios was applied to same weight gain, except for D where 50% coating suspension applied sample was studied for dissolution.

The results are illustrated in Table 11 below. The release of albuterol sulfate in the tablet according to the present invention was found to be too slow for comparison.

TABLE 11

|  | Time, Hrs | | | | | |
| --- | --- | --- | --- | --- | --- | --- |
|  | 1 | 2 | 4 | 6 | 8 | 10 |
| A(10:90) | 0 | 0 | 0 | 0 | 0 | 0 |
| B(20:80) | 0 | 0 | 0 | 0 | 0 | 0 |
| C(30:70) | 0 | 0 | 0 | 0 | 0 | 1 |
| D(35:65), 50% | 1 | 4 | 34 | 59 | 76 | 87 |
| Volmax ®, 4 mg | 8 | 22 | 47 | 69 | 87 | 92 |

Example 8

Dissolution Profiles of Volmax® Tablets 4 and 8 mg Volmax® tablets were subjected to dissolution testing according to the dissolution procedure set forth herein, with the exception that 12 tablets were tested for the 4 mg tablet whereas 6 tablets were tested for the 8 mg tablets. Solutions of different pH were prepared according to USP 25. The data for the tests using 0.90% NaCl were obtained from outside data. The dissolution results are shown in Tables 12 and 13 below.

TABLE 12

Dissolution Profile of Volmax ® tablet, 4 mg in Various Media.
Method: USP 23, 2 (paddle) at 50 RPM, 900 M, 37° C. (12 Tablets)

| | %, Dissolved | | | | | | |
|---|---|---|---|---|---|---|---|
| Medium | 1 hour | 2 hours | 4 hours | 6 hours | 8 hours | 10 hours | Recovery |
| PH 1.2 buffer | 11 | 26 | 56 | 81 | 92 | 96 | 98 |
| PH 4.5 buffer | 12 | 29 | 59 | 83 | 92 | 95 | 97 |
| PH 6.4 buffer | 12 | 28 | 58 | 82 | 92 | 95 | 98 |
| PH 7.4 buffer | 11 | 26 | 53 | 77 | 90 | 94 | 97 |
| 0.90% NaCl | 11 | 25 | 53 | 76 | 91 | 95 | 99 |

TABLE 13

Dissolution Profile of Volmax ® tablet, 8 mg in Various Media.
Method: USP 23, 2 (paddle) at 50 RPM, 900 M, 37° C. (6 Tablets)

| | %, Dissolved | | | | | | |
|---|---|---|---|---|---|---|---|
| Medium | 1 hour | 2 hours | 4 hours | 6 hours | 8 hours | 10 hours | Recovery |
| PH 1.2 buffer | 12 | 25 | 52 | 78 | 92 | 96 | 99 |
| PH 4.5 buffer | 12 | 27 | 56 | 80 | 92 | 94 | 96 |
| PH 6.4 buffer | 13 | 30 | 60 | 86 | 93 | 95 | 98 |
| PH 7.4 buffer | 12 | 27 | 53 | 78 | 92 | 95 | 97 |
| 0.90% NaCl | 11 | 25 | 52 | 78 | 93 | 98 | 101 |

Example 9

4 and 8 mg tablets according to Example 1 were subjected to controlled accelerated conditions of 40° C. and 75% Relative Humidity for indication of the stability of tablets according to the present invention. The results are shown in Tables 14 and 15.

TABLE 14

Stability data of Albuterol Sulfate ER tablets, 8 mg
Condition: 40° C./75% RH

| | | 100's | | | 500's | | |
|---|---|---|---|---|---|---|---|
| Drug Release, % | Initial | 1 month | 2 month | 3 month | 1 month | 2 month | 3 month |
| 1st hour | 3 | 2 | 3 | 2 | 2 | 2 | 2 |
| 2nd hour | 19 | 20 | 22 | 18 | 21 | 21 | 19 |
| 4th hour | 50 | 48 | 48 | 46 | 49 | 48 | 47 |
| 6th hour | 69 | 68 | 67 | 65 | 69 | 67 | 66 |
| 8th hour | 83 | 81 | 85 | 78 | 83 | 80 | 81 |
| 10th hour | 92 | 87 | 87 | 88 | 90 | 89 | 87 |
| Assay, % | 98.2 | 98.0 | 98.3 | 97.0 | 98.2 | 98.0 | 97.5 |
| Moisture, % | 3.6 | 3.8 | 3.7 | 3.8 | 3.7 | 3.8 | 3.6 |

TABLE 15

Stability data of Albuterol Sulfate ER tablets, 4 mg
Condition: 40° C./75% RH

| Drug Release, % | Initial | 100's | | | 500's | | |
|---|---|---|---|---|---|---|---|
| | | 1 month | 2 month | 3 month | 1 month | 2 month | 3 month |
| $2^{nd}$ hour | 9 | 7 | 7 | 3 | 7 | 6 | 7 |
| $4^{th}$ hour | 45 | 43 | 41 | 39 | 43 | 40 | 43 |
| $6^{th}$ hour | 65 | 65 | 61 | 61 | 65 | 61 | 64 |
| $8^{th}$ hour | 79 | 80 | 77 | 76 | 79 | 76 | 78 |
| $10^{th}$ hour | 88 | 89 | 86 | 86 | 88 | 86 | 88 |
| Assay, % | 98.9 | 98.7 | 97.2 | 98.2 | 98.8 | 97.6 | 98.6 |
| Moisture, % | 3.4 | 3.3 | 3.4 | 3.4 | 3.4 | 3.4 | 3.3 |

Example 10

This example is directed to bioequivalence study of both 4 & 8 mg products under fed and fasting conditions in healthy subjects.

The objective of the clinical study was to compare the relative steady state bioavailability of Sidmak products with Reference products. The study design was comparative randomized 2 way crossover steady state studies of Sidmak and Muro (Volmax) 4 and 8 mg Albuterol Sulfate Extended Release tablets in healthy adult males under fed and fasting conditions. Clinical supplies for the test product according to the present invention were according to Example 1, and Reference Product, Volmax manufactured by Glaxo Wellcome were Lot No: 10460727 for 8 mg tablets and Lot No. D008194 for 4 mg tablets.

Blood samples were collected during each study period before the initial drug administration and up to 12 hours post dose at appropriate times. Overall, data for the number of subjects indicated in the tables were analyzed in accordance with FDA guidance "Bioavailability and Bioequivalence Studies for Orally administered Drug Products—General Considerations.

Albuterol ion plasma was analyzed using a validated LC/MS/MS method developed at MDS Pharma Services, Inc. The following Pharmacokinetic parameters for plasma Albuterol were calculated.

| | |
|---|---|
| AUC 0-t | The area under the plasma concentration versus time curve, from time 0 to the last measurable concentration, as calculated by the linear trapezoidal method. |
| AUCinf | The area under the plasma concentration versus time curve from time 0 to infinity. AUCinf was calculated as the sum of the AUC 0-t plus the ratio of the last measurable plasma concentration to the elimination rate constant. |
| AUC/AUCinf | The ratio of AUC 0-t to AUCinf. |
| Cmax | Maximum measured plasma concentration over the time span Specified. |
| tmax | Time of the maximum measured plasma concentration. If the maximum value occurred at more than one time point, tmax was defined as the 1st time point with this value. |
| kel: | Apparent first-order terminal elimination rate constant calculated from a semi-log plot of the plasma concentration versus time curve. The parameter was calculated by linear least-squares regression analysis using the last three (or more) non-zero plasma concentrations. |
| T½ | The apparent first-order terminal elimination half-life is calculated as 0.693/kel |

Statistical analysis was performed using ANOVA on the transformed AUC 0-t; AUC inf; and Cmax pharmacokinetic parameters.

| | Albuterol | |
|---|---|---|
| Parameter | Sidmak Fed Vs Fasting | Sidmak Fed Vs. Muro Fed |
| AUC 0-t | 97.6% | 97.3% |
| AUC inf | 97.7% | 97.1% |
| Cmax | 78.5% | 98.8% |

Whereas, the following data was obtained under steady state fasting conditions

| Parameter | Albuterol |
|---|---|
| ln AUC 0-t | 99.1% (95–103.3%) |
| ln Cmax | 104.8%(98.2–111.8%) |

The ratios of LSM, least square means, and 90% confidence intervals for the ln-transformed parameters AUC and Cmax were within the 80–125% FDA acceptance range Based on these results, the present invention and Muro 4 and 8 mg albuterol sulfate extended release tablets are bioequivalent under fed as well as steady state fasting conditions.

Figure 2:
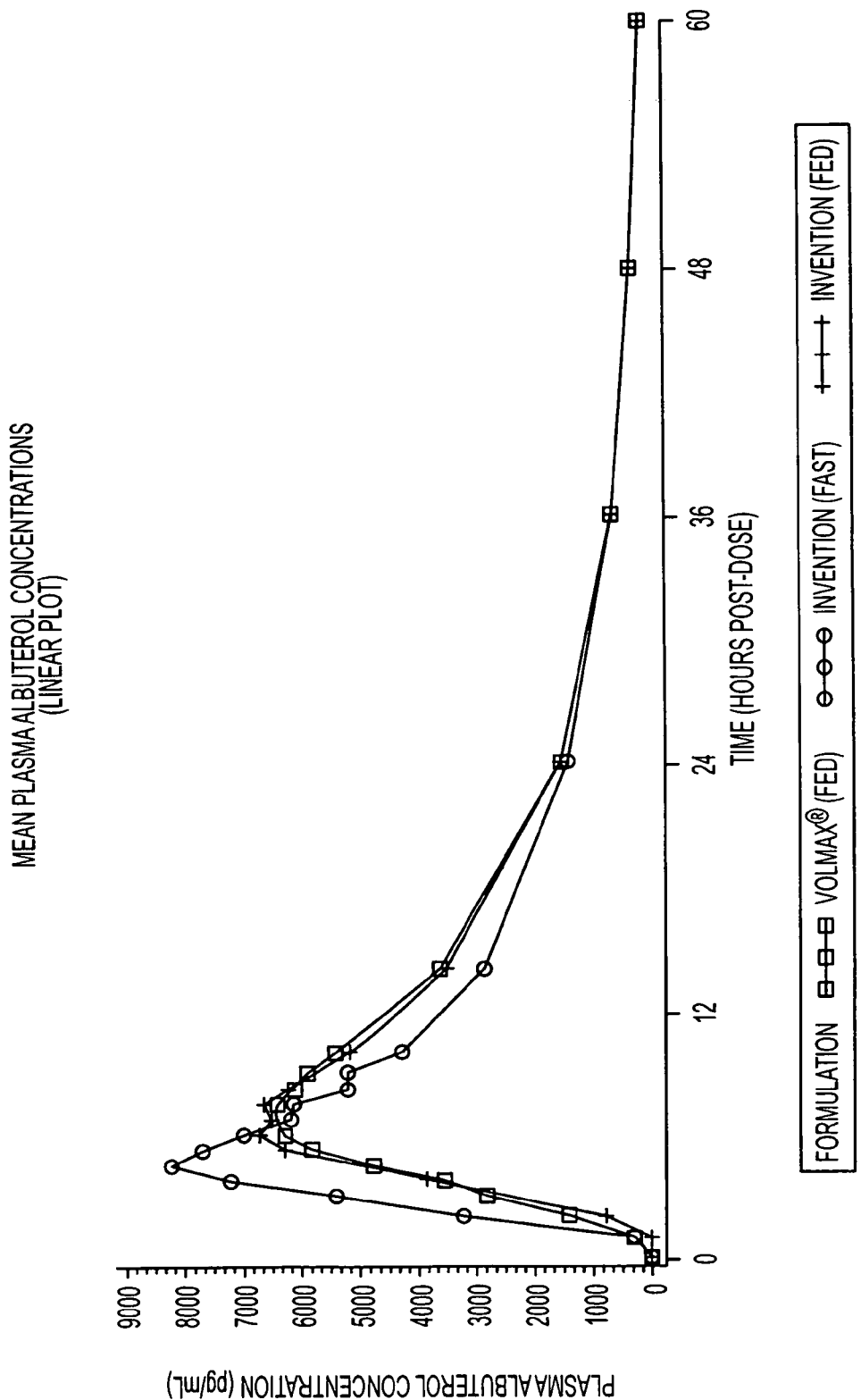
FIG. 2 shows a linear plot of mean plasma albuterol concentrations for plasma albuterol concentration vs. time for data shown in Table 16.
Figure 3:
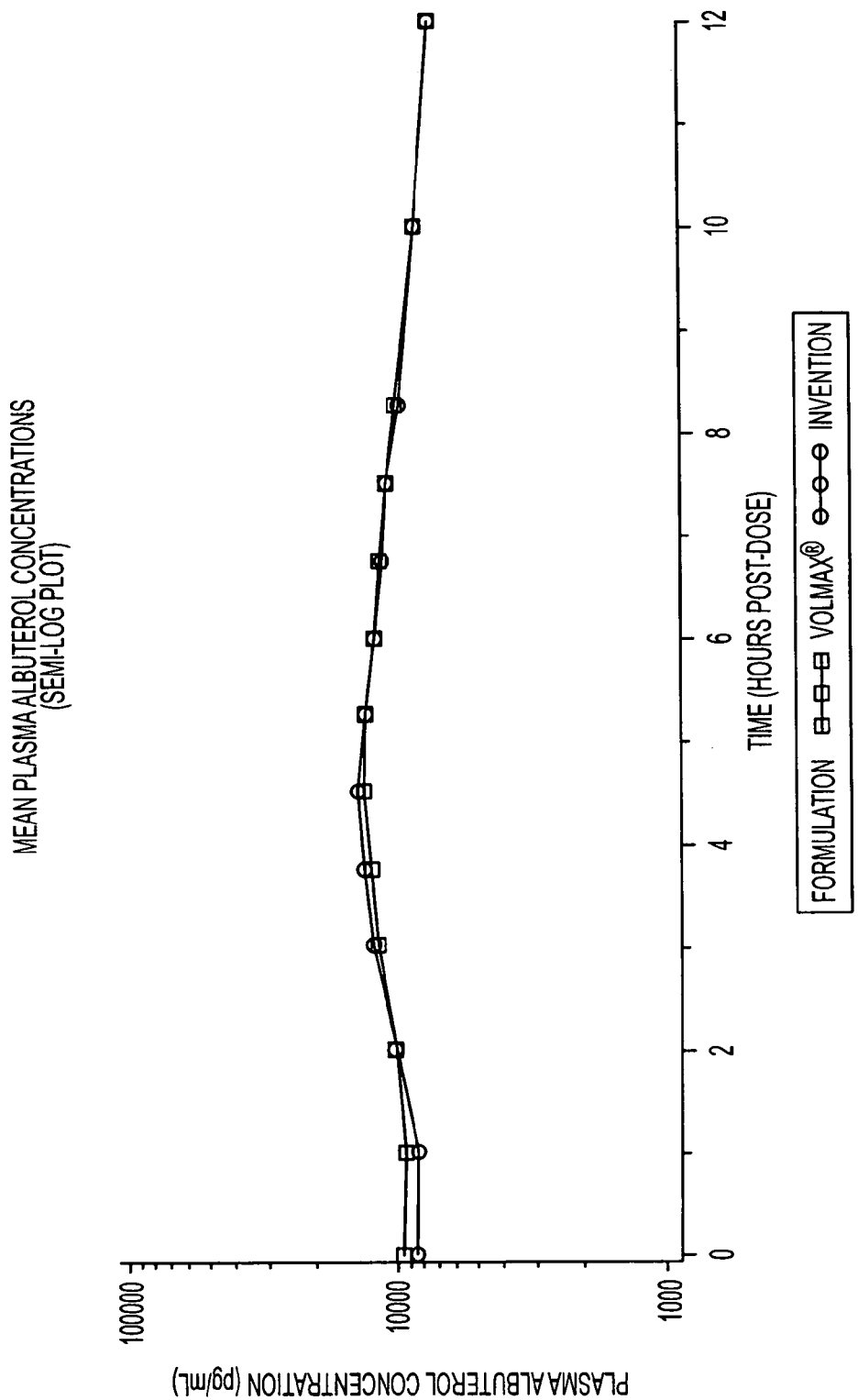
FIG. 3 shows a semi-log plot of mean plasma albuterol concentrations for plasma albuterol concentration vs. time for data shown in Table 17.
Figure 4:
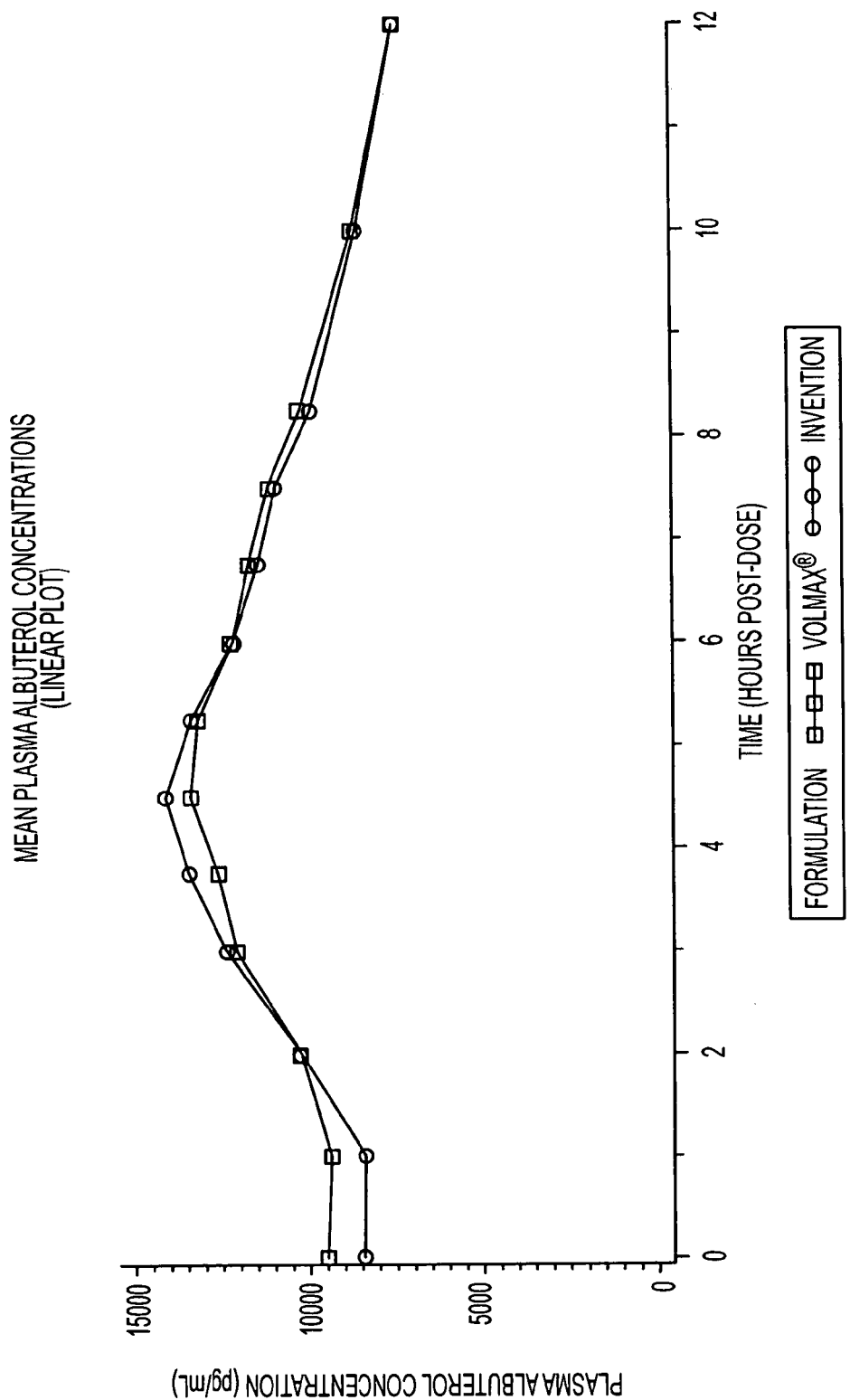
FIG. 4 shows a linear plot of mean plasma albuterol concentrations for plasma albuterol concentration vs. time for data shown in Table 17.

Table 16 and FIGS. 1 and 2, and Table 17 and FIGS. 3 and 4 identify the data under each study for 8 mg product.

Figure 5:
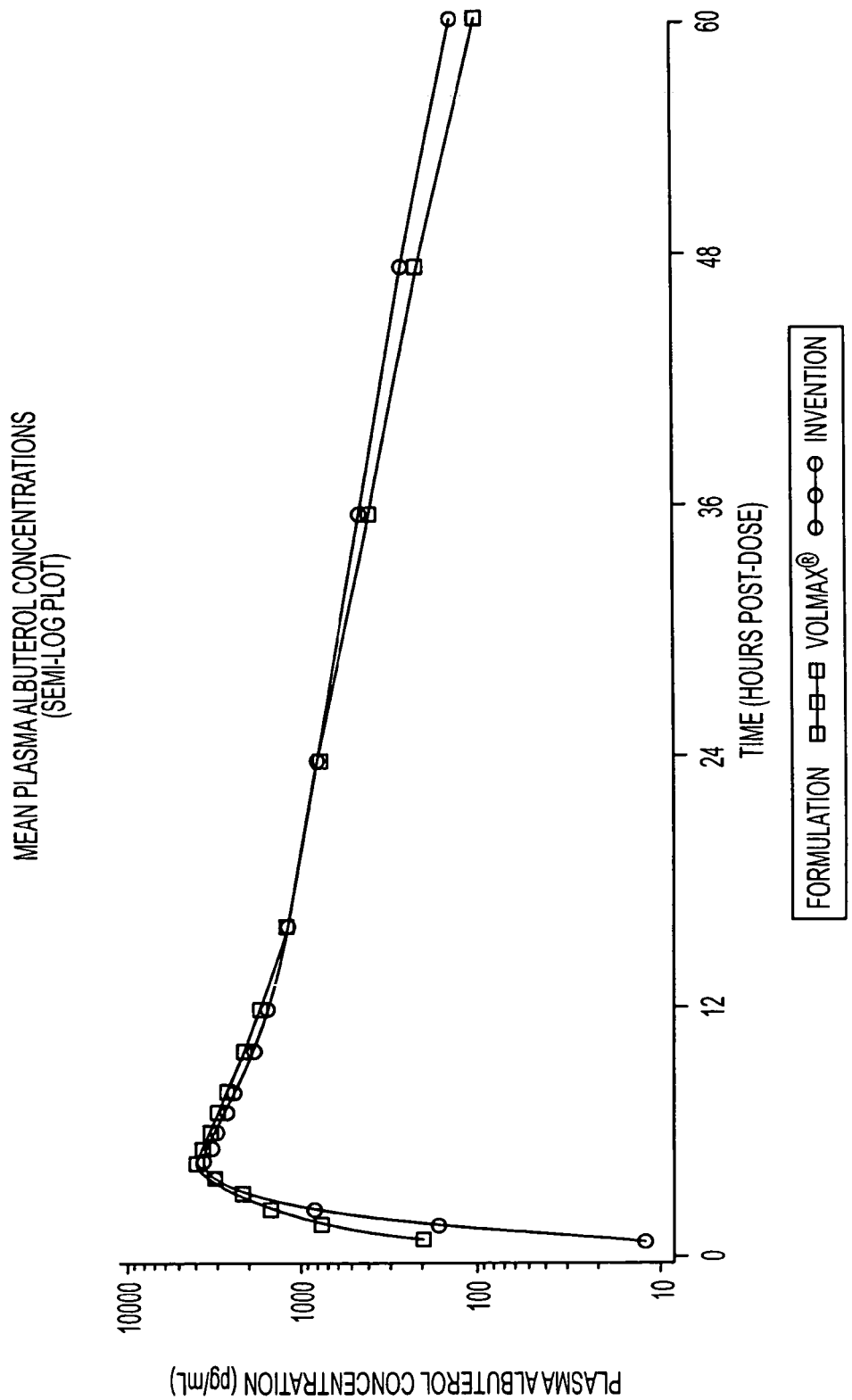
FIG. 5 shows a semi-log plot of mean plasma albuterol concentrations for plasma albuterol concentration vs. time for data shown in Table 18.
Figure 6:
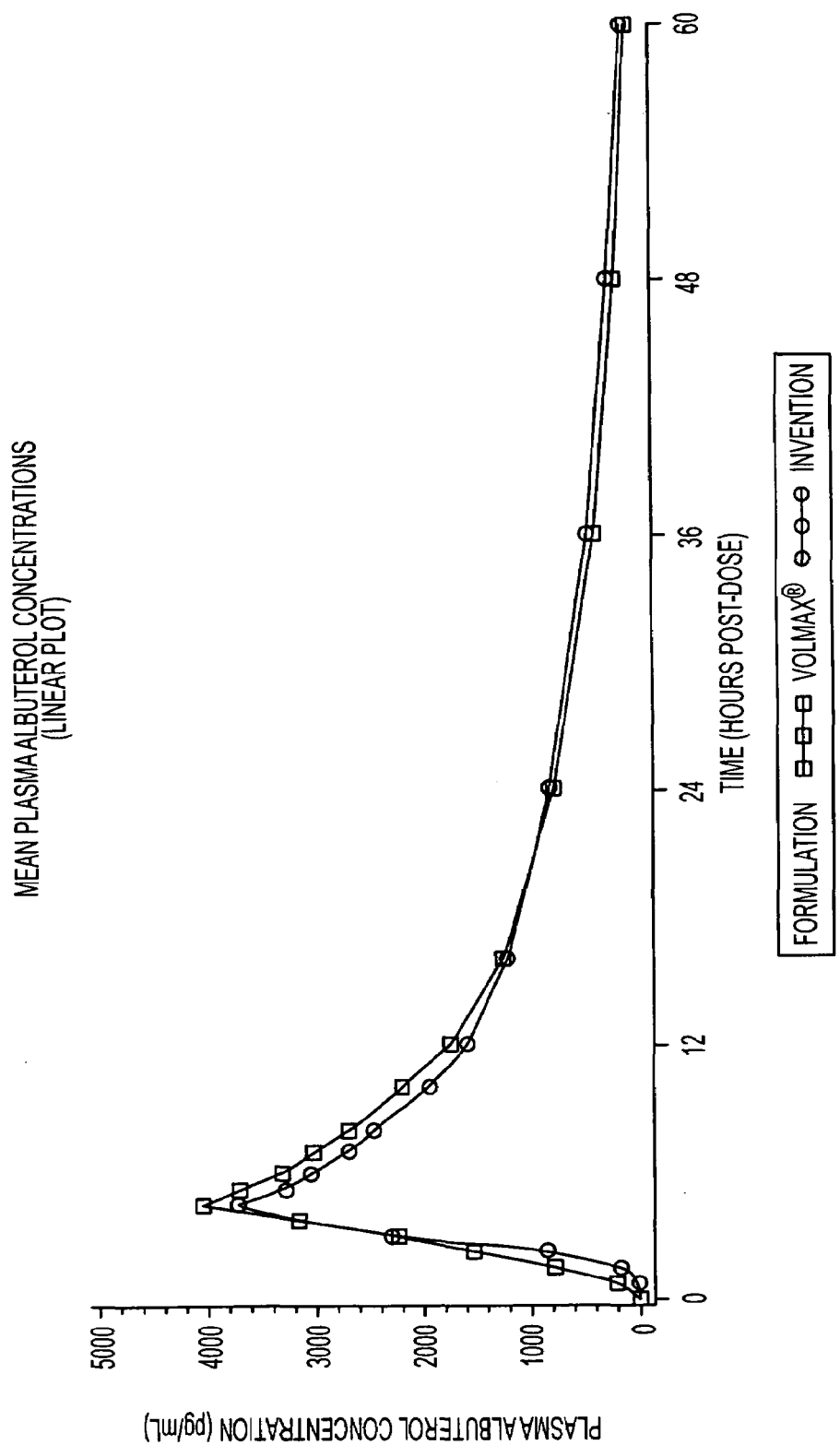
FIG. 6 shows a linear plot of mean plasma albuterol concentrations for plasma albuterol concentration vs. time for data shown in Table 18.

Similar studies were conducted using 4 mg of the invention product and compared with Muro 4 mg Albuterol sulfate extended release products. Table 18 and FIGS. 5 and 6 identify the data under each study for 4 mg product.

TABLE 16

Summary of Results - Albuterol in Plasma
Pharmacokinetic Parameters
(N = 17)

| | ln AUC 0-t* (pg · h/mL) | ln AUCinf* (pg · h/mL) | ln Cmax* (pg/mL) | tmax (h) | Half-life (h) | kel (1/h) |
|---|---|---|---|---|---|---|
| Sidmak (fast) (A) | | | | | | |
| Mean | 105616.66 | 109041.13 | 9075.487 | 4.556 | 11.958 | 0.06393 |
| CV | 23.5 | 23.8 | 29.5 | 33.5 | 32.0 | 32.2 |
| n | 17 | 17 | 17 | 17 | 17 | 17 |
| Sidmak (fed) (B) | | | | | | |
| Mean | 102950.39 | 106529.81 | 7081.606 | 6.691 | 11.839 | 0.06759 |
| CV | 28.9 | 28.8 | 35.0 | 34.6 | 42.9 | 35.1 |
| n | 17 | 17 | 17 | 17 | 17 | 17 |
| Kuro (fed) (C) | | | | | | |
| Mean | 106138.68 | 109692.47 | 7149.817 | 7.526 | 11.420 | 0.07171 |
| CV | 16.4 | 16.8 | 17.7 | 20.7 | 51.6 | 36.4 |
| n | 16 | 16 | 16 | 16 | 16 | 16 |
| Least-Squares Means | | | | | | |
| Sidmak (fast) (A) | 105313.16 | 108875.04 | 9001.416 | | | |
| Sidmak (fed) (B) | 102747.86 | 106368.82 | 7066.553 | | | |
| Muro (fed) (C) | 105608.89 | 109554.92 | 7155.965 | | | |
| Ratio of Least-Squares Means | | | | | | |
| (B/A) % | 97.6 | 97.7 | 78.5 | | | |
| (B/C) % | 97.3 | 97.1 | 98.8 | | | |

*For ln-transformed parameters, the antilog of the mean (i.e. the geometric mean) is reported.
Subject No. 13 did not complete period 3, Formulation C
PhAST STAB 2.3-000

TABLE 17

Summary of Results - Albuterol in Plasma
Pharmacokinetic Parameters
(N = 36)

| | ln AUC 0-t* (pg · h/mL) | ln Cmax* (pg/mL) | Cssav (pg/ml) | Cmin (pg/mL) | tmax (h) | Flux1 (%) | Flux2 (%) |
|---|---|---|---|---|---|---|---|
| Sidmak (A) | | | | | | | |
| Mean | 123488.78 | 15201.994 | 10539.18 | 7462.51 | 4.276 | 78.16 | 113.95 |
| CV | 22.9 | 21.6 | 21.5 | 25.7 | 20.7 | 23.3 | 31.3 |
| n | 36 | 36 | 36 | 36 | 36 | 36 | 36 |
| Kuro (B) | | | | | | | |
| Mean | 125572.85 | 14521.762 | 10693.54 | 7508.92 | 4.576 | 70.77 | 103.02 |
| CV | 21.7 | 21.4 | 20.6 | 22.3 | 26.1 | 25.6 | 31.4 |
| n | 35 | 36 | 35 | 35 | 36 | 35 | 35 |
| Least-Squares Means | | | | | | | |
| Sidmak (A) | 126622.28 | 15431.180 | | | | | |
| Kuro (B) | 127783.42 | 14726.983 | | | | | |
| Ratio of Least-Squares Means | | | | | | | |
| (A/B) % | 99.1 | 104.8 | | | | | |
| 90% Confidence Intervals (A/B) % | | | | | | | |
| lower limit: | 95.0% | 98.2% | | | | | |
| upper limit: | 103.3% | 111.8% | | | | | |
| p-value (ANOVA) | | | | | | | |
| A vs B | 0.7149 | 0.2319 | | | | | |
| Intrasubject CV % | 10.2 | 16.1 | | | | | |

*For ln-transformed parameters, the antilog of the mean (i.e. the geometric mean) is reported.
For Subject No. 37, period 2, formulation B, parameters AUC 0-t, Cssav, Cmin, Flux1 and Flux2 could not be calculated
PhAST STAB 2.3-000

TABLE 18

Summary of Results - Albuterol in Plasma Pharmacokinetic Parameter (N = 36)

|  | In AUC 0-t* (pg · h/mL) | In AUCinf* (pg · h/mL) | In Cmax* (pg/mL) | tmax (h) | Half-life (h) | kel (1/h) |
|---|---|---|---|---|---|---|
| Sidmak (A) | | | | | | |
| Mean | 51116.63 | 54777.81 | 4237.615 | 4.458 | 14.297 | 0.05633 |
| CV | 20.7 | 22.8 | 32.0 | 27.4 | 41.0 | 37.6 |
| n | 36 | 36 | 36 | 36 | 36 | 36 |
| Kuro (B) | | | | | | |
| Mean | 53073.89 | 55606.14 | 4383.472 | 4.660 | 12.614 | 0.06426 |
| CV | 20.3 | 21.1 | 26.5 | 20.3 | 42.8 | 38.0 |
| n | 36 | 36 | 36 | 36 | 36 | 36 |
| Least-Squares Means | | | | | | |
| Sidmak (A) | 51116.63 | 54777.81 | 4237.615 | | | |
| Kuro (B) | 53073.89 | 55606.14 | 4383.472 | | | |
| Ratio of Least-Squares Means (A/B) % | 96.3 | 98.5 | 96.7 | | | |
| 90% Confidence Intervals (A/B) % | | | | | | |
| lower limit: | 92.0% | 94.1% | 87.7% | | | |
| upper limit: | 100.8% | 103.1% | 106.6% | | | |
| p-Value (ANOVA) | | | | | | |
| A vs B | 0.1715 | 0.5816 | 0.5613 | | | |
| Period | 0.0267 | 0.0262 | 0.5056 | | | |
| Sequence | 0.0356 | 0.0782 | 0.4380 | | | |
| Intrasubject CV % | 11.4 | 11.5 | 24.8 | | | |

*For ln-transformed parameters, the antilog of the mean (i.e. the geometric mean) is reported.
See Section 3 of Report for details on calculation of parameters.
PhAST STAB 2.3-000

Example 11

Dissolution Examples at Differing pH 4 mg and 8 mg albuterol sulfate extended release tablets were prepared according Example 1. These tablets according to the invention, and Volmax® 4 and 8 mg tablets were studied using the dissolution procedure set forth above for 12 tablets. The tablets were dissolved in (900 ml) deionized water, 0.1 N HCl, pH buffer 4.5 and pH Buffer 6.8 prepared according to USP 25. Samples were taken at 1, 2, 4, 6 8 and 10 hours. The results are shown in Tables 19–22 for 4 mg tablets, and Tables 23–26 for 8 mg tablets.

TABLE 19

% OF LABEL CLAIM RELEASED AT SPECIFIED TIME INTERVAL IN DEIONIZED WATER

| | 4 mg Tablet of Invention | | | | | | | 4 mg Volmax ® Tablet | | | | | | |
|---|---|---|---|---|---|---|---|---|---|---|---|---|---|---|
| Unit # | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Min. | 111.2 | 2 | 20 | 52 | 70 | 82 | 91 | 86.4 | 11 | 23 | 46 | 66 | 87 | 91 |
| Max. | 117.9 | 3 | 30 | 62 | 78 | 89 | 96 | 90.5 | 15 | 33 | 65 | 92 | 96 | 96 |
| Avg. | 115.0 | 2 | 24 | 56 | 74 | 86 | 92 | 88.8 | 13 | 27 | 55 | 81 | 91 | 94 |
| % RSD | 2.0 | 27.2 | 13.4 | 5.1 | 3.2 | 2.3 | 1.4 | 1.4 | 12.4 | 10.7 | 10.1 | 8.2 | 2.6 | 1.7 |

TABLE 20

% OF LABEL CLAIM RELEASED AT SPECIFIED TIME INTERVAL IN 0.1 N HC

| Unit # | 4 mg Tablet of Invention | | | | | | | 4 mg Volmax ® Tablet | | | | | | |
|---|---|---|---|---|---|---|---|---|---|---|---|---|---|---|
| | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Min. | 113.3 | 2 | 9 | 53 | 72 | 84 | 90 | 89.2 | 8 | 21 | 43 | 62 | 84 | 92 |
| Max | 117.5 | 4 | 28 | 60 | 78 | 89 | 96 | 93.5 | 13 | 27 | 53 | 81 | 94 | 98 |
| Avg. | 115.1 | 3 | 19 | 56 | 75 | 87 | 93 | 91.3 | 11 | 24 | 49 | 72 | 90 | 95 |
| % RSD | 1.2 | 19.8 | 30.2 | 3.8 | 2.3 | 1.7 | 2.2 | 1.6 | 15.0 | 7.6 | 6.5 | 7.3 | 3.2 | 2.1 |

TABLE 21

% OF LABEL CLAIM RELEASED AT SPECIFIED TIME INTERVAL IN pH 4.5 BUFFER

| Unit # | 4 mg Tablet of Invention | | | | | | | 4 mg Volmax ® Tablet | | | | | | |
|---|---|---|---|---|---|---|---|---|---|---|---|---|---|---|
| | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Min. | 114.0 | 1 | 5 | 44 | 66 | 79 | 87 | 85.9 | 10 | 22 | 44 | 63 | 86 | 90 |
| Max | 119.6 | 2 | 21 | 52 | 71 | 83 | 91 | 91.9 | 14 | 32 | 64 | 89 | 98 | 99 |
| Avg. | 116.5 | 2 | 15 | 49 | 68 | 81 | 89 | 89.7 | 12 | 26 | 52 | 77 | 91 | 94 |
| % RSD | 1.2 | 28.3 | 34.8 | 4.5 | 2.4 | 1.5 | 1.4 | 2.2 | 8.6 | 10.8 | 10.7 | 11.2 | 4.2 | 2.5 |

TABLE 22

% OF LABEL CLAIM RELEASED AT SPECIFIED TIME INTERVAL IN pH 6.8 BUFFER

| Unit # | 4 mg Tablet of Invention | | | | | | | 4 mg Volmax ® Tablet | | | | | | |
|---|---|---|---|---|---|---|---|---|---|---|---|---|---|---|
| | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Min. | 113.2 | 1 | 3 | 37 | 58 | 72 | 81 | 87.5 | 9 | 20 | 39 | 57 | 75 | 87 |
| Max | 120.6 | 1 | 12 | 46 | 65 | 78 | 87 | 92.6 | 12 | 26 | 52 | 81 | 92 | 96 |
| Avg. | 115.6 | 1 | 6 | 42 | 62 | 75 | 85 | 90.3 | 11 | 23 | 46 | 68 | 87 | 92 |
| % RSD | 1.9 | 25.6 | 56.0 | 6.0 | 3.6 | 2.6 | 2.3 | 1.8 | 8.7 | 8.7 | 9.2 | 11.4 | 5.7 | 2.7 |

TABLE 23

% OF LABEL CLAIM RELEASED AT SPECIFIED TIME INTERVAL IN DEIONIZED WATER

| Unit # | 8 mg Tablet of Invention | | | | | | | 8 mg Volmax ® Tablet | | | | | | |
|---|---|---|---|---|---|---|---|---|---|---|---|---|---|---|
| | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Min. | 108.8 | 3 | 29 | 58 | 77 | 88 | 94 | 162.0 | 12 | 28 | 56 | 77 | 84 | 82 |
| Max | 113.6 | 13 | 36 | 66 | 85 | 95 | 99 | 175.3 | 15 | 37 | 72 | 94 | 99 | 99 |
| Avg. | 111.4 | 9 | 32 | 62 | 80 | 91 | 96 | 172.2 | 13 | 33 | 62 | 85 | 93 | 95 |
| % RSD | 1.3 | 32.2 | 6.3 | 3.6 | 2.8 | 2.2 | 1.7 | 2.2 | 8.6 | 9.9 | 8.1 | 6.1 | 4.2 | 4.9 |

TABLE 24

% OF LABEL CLAIM RELEASED AT SPECIFIED TIME INTERVAL IN 0.1 N HCl

| Unit # | 8 mg Tablet of Invention | | | | | | | 8 mg Volmax ® Tablet | | | | | | |
|---|---|---|---|---|---|---|---|---|---|---|---|---|---|---|
| | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Min. | 110.0 | 3 | 28 | 58 | 76 | 87 | 94 | 168.4 | 8 | 22 | 45 | 66 | 79 | 76 |
| Max | 115.2 | 11 | 37 | 66 | 84 | 94 | 99 | 182.8 | 14 | 30 | 61 | 87 | 96 | 99 |

TABLE 24-continued

% OF LABEL CLAIM RELEASED AT SPECIFIED TIME INTERVAL IN 0.1 N HCl

| | 8 mg Tablet of Invention | | | | | | | 8 mg Volmax ® Tablet | | | | | | |
|---|---|---|---|---|---|---|---|---|---|---|---|---|---|---|
| Unit # | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Avg. | 112.1 | 7 | 32 | 63 | 81 | 91 | 97 | 174.8 | 11 | 26 | 54 | 78 | 91 | 95 |
| % RSD | 1.2 | 38.8 | 7.5 | 4.2 | 3.0 | 2.2 | 1.6 | 2.2 | 16.2 | 11.1 | 8.5 | 7.2 | 5.0 | 6.6 |

TABLE 25

% OF LABEL CLAIM RELEASED AT SPECIFIED TIME INTERVAL IN pH 4.5 BUFFER

| | 8 mg Tablet of Invention | | | | | | | 8 mg Volmax ® Tablet | | | | | | |
|---|---|---|---|---|---|---|---|---|---|---|---|---|---|---|
| Unit # | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Min. | 107.6 | 2 | 24 | 52 | 70 | 84 | 91 | 166.9 | 11 | 22 | 46 | 67 | 88 | 91 |
| Max | 113.8 | 9 | 30 | 59 | 78 | 91 | 97 | 178.7 | 15 | 35 | 70 | 91 | 98 | 99 |
| Avg. | 111.1 | 5 | 27 | 55 | 74 | 86 | 94 | 173.5 | 13 | 30 | 59 | 82 | 92 | 95 |
| % RSD | 1.8 | 55.2 | 8.1 | 4.1 | 3.1 | 2.3 | 1.7 | 1.7 | 12.9 | 12.6 | 10.9 | 8.2 | 3.1 | 2.3 |

TABLE 26

% OF LABEL CLAIM RELEASED AT SPECIFIED TIME INTERVAL IN pH 6.8 BUFFER

| | 8 mg Tablet of Invention | | | | | | | 8 mg Volmax ® Tablet | | | | | | |
|---|---|---|---|---|---|---|---|---|---|---|---|---|---|---|
| Unit # | Unit Weight (mg) | 1 Hour | 2 Hours | 4 Hours | 6 Hours | 8 Hours | 10 Hours | Unit Weight (mg) | 1 Hour | 2 Hours | 4 Hours | 6 Hours | 8 Hours | 10 Hours |
| Min. | 107.8 | 1 | 17 | 43 | 61 | 74 | 84 | 162.2 | 10 | 21 | 45 | 68 | 87 | 91 |
| Max | 116.0 | 6 | 27 | 53 | 71 | 83 | 91 | 181.9 | 15 | 34 | 68 | 89 | 96 | 100 |
| Avg. | 111.0 | 2 | 22 | 49 | 67 | 80 | 88 | 173.4 | 12 | 27 | 57 | 80 | 92 | 96 |
| % RSD | 2.1 | 54.6 | 11.9 | 5.2 | 3.9 | 3.2 | 2.3 | 3.0 | 12.8 | 12.3 | 9.5 | 6.3 | 2.7 | 2.8 |

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. An extended release tablet comprising:
    a core including albuterol sulfate and extended release agent, said extended release agent comprising an extended release agent hydrophobic polymer comprising ethyl cellulose; and
    an extended release coating associated with the core to provide for sustained release of the albuterol sulfate, said extended release coating comprising a layer including extended release coating hydrophobic polymer comprising ethyl cellulose and hydrophilic polymer comprising methyl cellulose.

2. The extended release tablet according to claim 1 wherein ethanol is utilized as a solvent for preparing the core and the extended release coating.

3. The extended release tablet according to claim 1 wherein the core includes an anhydrous sulfate.

4. The extended release tablet according to claim 3 wherein the anhydrous sulfate comprises calcium sulfate.

5. The extended release tablet according to claim 1 wherein the core includes lactose monohydrate.

6. The extended release tablet according to claim 1 comprising an albuterol dissolution profile for a formulation containing 8 mg of albuterol of:

| | |
|---|---|
| 2$^{nd}$ Hour | Not more than 30% |
| 6$^{th}$ Hour | 50–75% |
| 10$^{th}$ Hour | Not less than 75%. |

7. The extended release tablet according to claim 1 comprising an albuterol dissolution profile for a formulation containing 4 mg of albuterol of:

| | |
|---|---|
| 2$^{nd}$ Hour | Not more than 20% |
| 6$^{th}$ Hour | 45–70% |
| 10$^{th}$ Hour | Not less than 75%. |

8. The extended release tablet according to claim 1 having bioequivalency to an albuterol sulfate osmotic device formulation.

9. An extended release tablet comprising:
a core including albuterol sulfate and extended release agent;
an extended release coating associated with the core to provide for sustained release of the albuterol sulfate, said extended release coating comprising a layer including extended release coating hydrophobic polymer and hydrophilic polymer; and
the hydrophobic polymer and the hydrophilic polymer of said extended release coating are present in a weight ratio of 55–65:45–35 of said extended release coating hydrophobic polymer to said hydrophilic polymer.

10. The extended release tablet according to claim 9 wherein the extended release agent comprises an extended release agent hydrophobic polymer.

11. The extended release tablet according to claim 10 wherein the extended release agent hydrophobic polymer comprises ethyl cellulose.

12. The extended release tablet according to claim 9 wherein the extended release coating hydrophobic polymer comprises ethyl cellulose, the hydrophilic polymer comprises methyl cellulose, and the extended release agent comprises an extended release hydrophobic polymer comprising ethyl cellulose.

13. The extended release tablet according to claim 9 wherein the hydrophobic polymer and hydrophilic polymer of said extended release coating are present in a weight ratio of 57:43 of said extended release coating hydrophobic polymer to said hydrophilic polymer.

14. The extended release tablet according to claim 9 wherein the hydrophobic polymer and hydrophilic polymer of said extended release coating comprise ethyl cellulose and methyl cellulose, respectively.

15. The extended release tablet according to claim 13 wherein the hydrophobic polymer and hydrophilic polymer of said extended release coating comprise ethyl cellulose and methyl cellulose, respectively.

16. The extended release tablet according to claim 9 wherein the extended release coating has a weight of about 5 to 25 mg.

17. The extended release tablet according to claim 16 wherein the extended release coating has a weight of about 8 to 13 mg.

18. The extended release tablet according to claim 16 wherein the extended release coating hydrophobic polymer comprises ethyl cellulose and the hydrophilic polymer comprises methyl cellulose.

* * * * *